(12) United States Patent
Yuri et al.

(10) Patent No.: US 6,904,068 B2
(45) Date of Patent: Jun. 7, 2005

(54) SEMICONDUCTOR LASER DEVICE AND MULTIPLE WAVELENGTH LASER LIGHT EMITTING APPARATUS EMPLOYING THE SEMICONDUCTOR LASER DEVICE

(75) Inventors: Masaaki Yuri, Ibaraki (JP); Seiichiro Tamai, Osaka-fu (JP); Kunio Ito, Uji (JP); Masaru Kazumura, Takatsuki (JP)

(73) Assignee: Matsushita Electric Inustrial Co., Ltd., Osaka-fu (JP)

( * ) Notice: Subject to any disclaimer, the term of this patent is extended or adjusted under 35 U.S.C. 154(b) by 49 days.

(21) Appl. No.: 09/824,456

(22) Filed: Apr. 2, 2001

(65) Prior Publication Data

US 2001/0030983 A1 Oct. 18, 2001

(30) Foreign Application Priority Data

Mar. 31, 2000 (JP) ........................... 2000-099512
Mar. 31, 2000 (JP) ........................... 2000-099514

(51) Int. Cl.[7] ................................. H01S 3/13
(52) U.S. Cl. ..................... 372/29.023; 372/29.02; 372/92; 372/102; 372/108
(58) Field of Search ................ 372/29.023, 29.02, 372/32, 92, 99, 102, 96, 108, 69, 70, 75, 34, 36

(56) References Cited

U.S. PATENT DOCUMENTS

| | | | | |
|---|---|---|---|---|
| 4,006,487 A | * | 2/1977 | Allen | 396/155 |
| 4,266,549 A | | 5/1981 | Kimura | |
| 4,541,712 A | | 9/1985 | Whitney | |
| 4,686,485 A | | 8/1987 | Goldberg et al. | |
| 4,764,935 A | | 8/1988 | Wilcox et al. | |
| 4,831,630 A | | 5/1989 | Scifres et al. | |
| 4,868,839 A | | 9/1989 | Simmons et al. | |
| 5,274,657 A | | 12/1993 | Hori et al. | |
| 5,386,426 A | * | 1/1995 | Stephens | 372/20 |
| 5,487,725 A | | 1/1996 | Peyman | |
| 5,570,226 A | * | 10/1996 | Ota | 372/92 |
| 5,691,989 A | * | 11/1997 | Rakuljic et al. | 372/102 |
| 5,713,892 A | | 2/1998 | Shimmick | |
| 5,766,981 A | * | 6/1998 | Thornton et al. | 438/36 |
| 5,936,984 A | * | 8/1999 | Meissner et al. | 372/34 |
| 6,094,515 A | * | 7/2000 | Miki et al. | 385/31 |
| 6,167,075 A | * | 12/2000 | Craig et al. | 372/75 |
| 6,208,679 B1 | * | 3/2001 | Sanchez-Rubio et al. | 372/92 |
| 6,212,216 B1 | * | 4/2001 | Pillai | 372/99 |
| 6,327,293 B1 | * | 12/2001 | Salokatve et al. | 372/96 |
| 6,418,152 B1 | * | 7/2002 | Davis | 372/102 |

FOREIGN PATENT DOCUMENTS

| | | |
|---|---|---|
| DE | 33 30 293 | 3/1985 |
| DE | 42 34 342 | 4/1994 |
| EP | 0 301 846 | 2/1989 |
| EP | 0 331 235 | 9/1989 |
| EP | 0 625 846 | 11/1994 |
| JP | 62115795 | 5/1987 |

\* cited by examiner

*Primary Examiner*—Minsun Oh Harvey
*Assistant Examiner*—James Menefee

(57) ABSTRACT

To provide a semiconductor laser device that is capable of outputting high power laser light and is suitable for optical recording, optical communication, welding, and the like, and a multiple wavelength laser light emitting apparatus employing the semiconductor laser device. The semiconductor laser device includes an optical element that at least partially reflects a laser beam emitted from an end face of a laser light oscillator in a semiconductor laser array element so that the laser beam is incident on another laser light oscillator. Due to this, even when laser light oscillators are disposed with such a pitch that does not pose problems in manufacturing, a laser beam emitted from an end face of one laser light oscillator and a laser beam emitted from an end face of another laser light oscillator are phase-locked. By condensing these laser beams, the semiconductor laser device can output higher power laser light than conventional.

12 Claims, 19 Drawing Sheets

800

SEMICONDUCTOR LASER DEVICE AND MULTIPLE WAVELENGTH LASER LIGHT EMITTING APPARATUS EMPLOYING THE SEMICONDUCTOR LASER DEVICE

BACKGROUND OF THE INVENTION (1) Field of the Invention

The present invention relates to a high power semiconductor laser device that is capable of outputting laser light of high power and is suitable for optical recording, optical communication, welding, and the like, and to a multiple wavelength laser light emitting apparatus employing the high power semiconductor laser device.

(2) Related Art

In recent years, a great deal of research has been made to develop high power semiconductor laser devices used as light sources for optical recording, optical communication, welding, and the like.

One example of such semiconductor laser devices is disclosed in Japanese Laid-Open Patent Application No. H05-226765. A technique disclosed therein is for emitting laser light using a semiconductor laser array element as a light source, the semiconductor laser array element having an array structure in which a plurality of laser light oscillators are formed in stripes on one substrate.

According to this technique, the plurality of laser light oscillators are made close to each other on the substrate, so that energies filter through each of the laser light oscillators and are combined together, resulting in phases of laser beams emitted from end faces of the laser light oscillators being synchronized. Accordingly, the laser beams emitted from the end faces of the laser light oscillators can be easily condensed on one spot using an optical lens or the like, realizing output of high power laser light.

With the above technique, the laser light oscillators are connected to each other through the energies filtering through each of the laser light oscillators. However, such energies are spread in an extremely small range of some microns, and therefore, the laser light oscillators should be located extremely close to each other in a narrow space. This poses restrictions for the design of a semiconductor laser device, such that a width of a current blocking layer is to be made narrow, making manufacturing of such a semiconductor laser device extremely difficult. Also, as the laser light oscillators are located close to each other, heat is confined within narrow spaces, making heat generation more active. Rise in temperatures is particularly remarkable at the central part of the semiconductor laser device, which might cause dissolution or thermal expansion of the semiconductor laser device, the thermal expansion causing changes in the wavelength of laser beams. This could undermine reliability of the semiconductor laser device. Furthermore, this semiconductor laser device also lacks in stability as energies filter through the laser light oscillators unevenly. To avoid such problems, setting a width of a current blocking layer wider to make an interval between adjacent laser light oscillators larger can considered, in disregard of making phases of the laser beams synchronized. However, in this case, the laser beams can not be condensed on one spot, and accordingly output of high power laser light cannot be achieved.

Also, a plurality of such semiconductor laser array elements maybe used as a light source in an attempt to increase the total amount of light and achieve output of high power laser light. However, in this case, only a certain level of output can be achieved, because phases of laser beams emitted from one semiconductor laser array element cannot be synchronized with phases of laser beams emitted from other semiconductor laser array elements.

SUMMARY OF THE INVENTION

The present invention aims to provide a semiconductor laser device that is capable of outputting laser light of high power, even when laser light oscillators in the semiconductor laser device are arranged parallel to each other with such a pitch that does not pose problems in manufacturing the semiconductor laser device, by synchronizing wavelengths and phases of laser beams emitted from the laser light oscillators (synchronizing wavelength and phases is hereafter referred to as "phase-locking"). The present invention also aims to provide a multiple wavelength laser light emitting apparatus employing this semiconductor laser device.

The semiconductor laser device to which the present invention relates includes a plurality of laser light oscillators that each emit a laser beam from an outlet thereof; and an optical element that at least partially reflects, scatters, or transmits a laser beam that is oscillated in at least one of the laser light oscillators and is emitted from an outlet thereof, so that a portion of the laser beam is incident on at least one of the laser light oscillators.

With this construction, even when laser light oscillators are arranged with a large pitch, a laser beam emitted from an outlet of one laser light oscillator and a laser beam emitted from an outlet of another laser light oscillator are phase-locked, giving less restrictions for designing and manufacturing of the semiconductor laser device. By condensing the phase-locked laser beams, the semiconductor laser device realizes output of higher power laser light than conventional.

More specifically, the plurality of laser light oscillators may be included in a plurality of semiconductor laser array elements in such a manner that at least two laser light oscillators are included in each laser light oscillator in an array, the plurality of semiconductor laser array elements being stacked up, and the optical element is disposed so as to face the outlet of the at least one of the laser light oscillators included in one of the semiconductor laser array elements, the optical element being a translucent member that (a) partially transmits the laser beam and (b) partially reflects or scatters the laser beam so that a portion of the laser beam is directed to the at least one of the other laser light oscillators included in the other semiconductor laser array elements.

With this construction, laser beams emitted from the same laser light oscillator semiconductor laser array, as well as laser beams emitted from different laser light oscillators can be phase-locked.

The optical element may direct the portion of the laser beam to be incident on the at least one of the other laser light oscillators in the vicinity of the optical axis of the portion of the laser beam at an outlet of the laser light oscillator so that the laser beam is incident on the laser light oscillator. This makes phase-locking of laser beams occur more easily.

Also, the optical element may be a flat plate having a main surface that is either a flat plane or a scabrous plane, the main surface being an incidence plane of the laser beam, and the optical element partially reflects or scatters the laser beam on the main surface.

With this construction, the laser beam reflected or scattered by the optical element is incident on the at least one of the other laser light oscillators, so that the incident laser beams are phase-locked.

Also, the optical element may be a flat plate which includes a diffraction grating on a main surface thereof, the main surface being an incidence plane of the laser beam, and the optical element partially diffracts the laser beam on the diffraction grating at a predetermined angle when the optical element partially reflects the laser beam.

As this diffraction grating efficiently diffracts laser beams back to outlets of other laser light oscillators, the laser beams are more easily phase-locked.

More specifically, the optical element may direct −1st order diffracted light and +1st order diffracted light generated when the laser beam is partially diffracted, so as to be respectively incident on laser light oscillators that are adjacent to the at least one of the plurality of laser light oscillators from which the laser beam has been emitted.

Also, the optical element reflects or scatters the laser beam so as to be incident on the at least one of the other laser light oscillators included in the other semiconductor laser array elements.

With this construction, laser beams emitted from laser light oscillators included in the other semiconductor array elements can also be phase-locked.

Also, the optical element may be subjected to hologram processing so as to function as a hologram to condense or collimate a portion of the laser beam that has transmitted therethrough. By doing so, an optical element for such purposes does not need to be provided, making an apparatus employing the semiconductor laser device compact.

Also, the plurality of semiconductor laser array elements in the above semiconductor laser device each include a substrate layer that has been cut out of a semiconductor wafer. Here, it is preferable that each substrate layer is cut out of the same semiconductor laser device. By doing so, wavelengths of laser beams emitted from different semiconductor laser array elements become similar, and so the laser beams can be more easily phase-locked.

The above semiconductor laser array elements may each have a real refractive index guided self-aligned structure.

The multiple wavelength laser light emitting apparatus according to the present invention includes a plurality of semiconductor laser devices that each emits a plurality of laser beams, wavelengths of the laser beams emitted from each semiconductor laser device being different from wavelengths of the laser beams emitted from a different semiconductor laser device; and an optical element that condenses a plurality of laser beams emitted from each of the plurality of semiconductor laser devices at a predetermined position, wherein at least one of the semiconductor laser devices is the semiconductor laser device of the present invention.

With this construction, the multiple wavelength laser light emitting apparatus can output high power laser light with its construction being compact relative to a conventional one.

BRIEF DESCRIPTION OF THE DRAWINGS

These and other objects, advantages and features of the invention will become apparent from the following description thereof taken in conjunction with the accompanying drawings that illustrate a specific embodiment of the invention. In the drawings.

DESCRIPTION OF THE PREFERRED EMBODIMENTS

Figure 1:
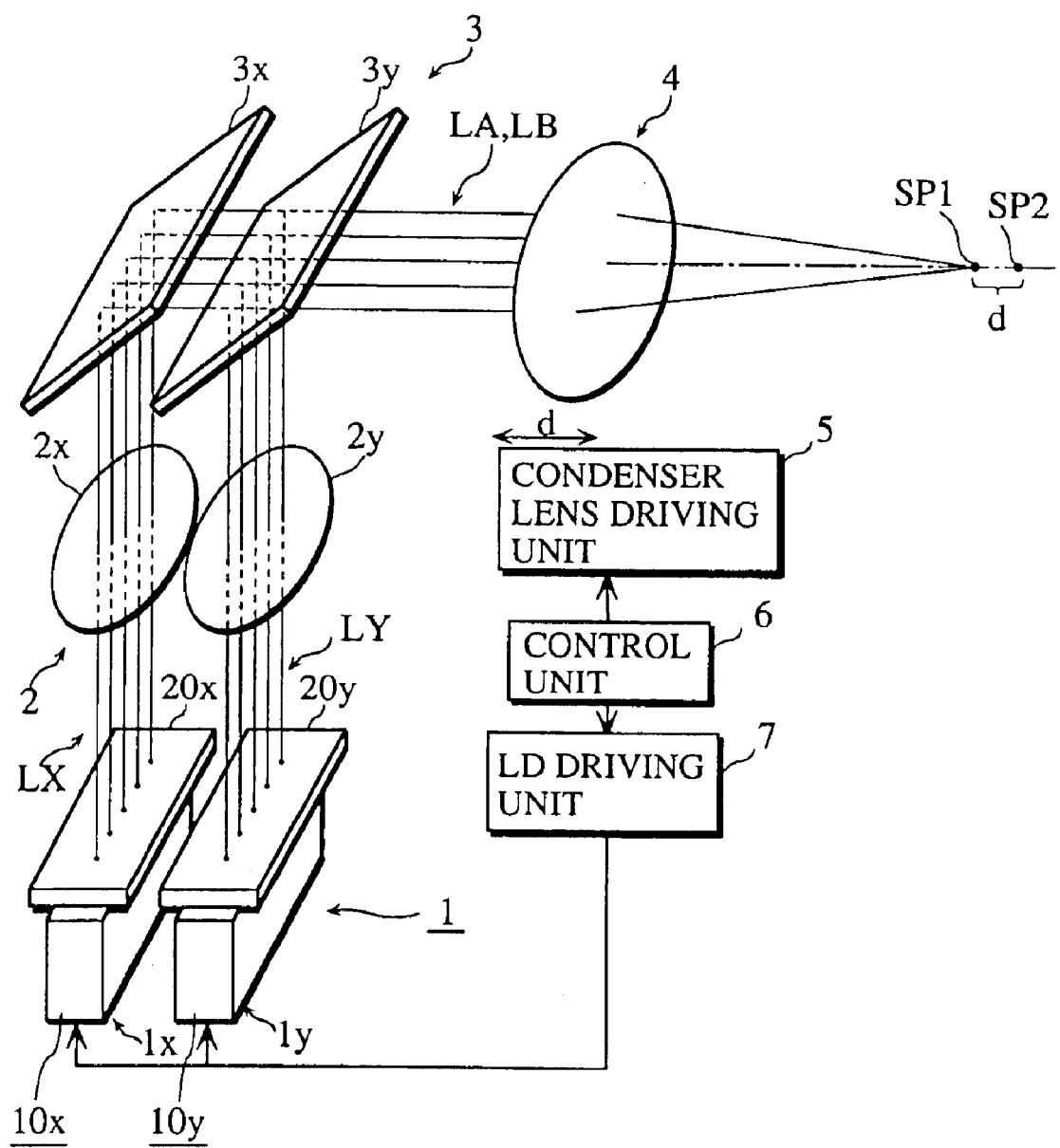
FIG. 1 is a perspective view of an overall construction of a multiple wavelength laser light emitting apparatus relating to a first embodiment of the present invention.

The following is an explanation of preferred embodiments of a semiconductor laser device of the present invention, with reference to the drawings.
First Embodiment
(1) Construction of Multiple Wavelength Laser Light Emitting Apparatus FIG. 1 schematically shows the construction of the main part of the multiple wavelength laser light emitting apparatus relating to the first embodiment of the present invention.

As shown in the figure, the multiple wavelength laser light emitting apparatus is roughly composed of a light source unit 1 that emits two types of laser beams LX (red) and laser beams LY (infrared), each type having a different wavelength, a collimator unit 2 that collimates the laser beams LX and LY emitted from the light source unit 1 so as to be collimated beams, a reflector unit 3 that reflects the laser beams LX and LY so as to travel in the same direction with being parallel to each other, a condenser lens 4 that condenses the laser beams LX and LY at a predetermined condensing position on the optical axis, a condenser lens driving unit 5 that drives the condenser lens 4 in the direction of the optical axis, and a control unit 6 that controls an operation of the condenser lens driving unit 5. It should be noted that the condenser lens may usually be composed of a plurality of lenses, however, a single lens, the condenser lens 4 is employed in the present embodiment.

The light source 1 is composed of a semiconductor laser device 1x and a semiconductor laser device 1y disposed being parallel to each other. The semiconductor laser devices 1x and 1y respectively emit a plurality of laser beams LX and a plurality of laser beams LY with being substantially parallel to each other, the laser beam LX and the laser beam LY each having a different wavelength.

The semiconductor laser devices 1x and 1y respectively include semiconductor laser array elements 10x and 10y, and optical elements 20x and 20y. The optical elements 20x and 20y partially reflect laser beams emitted from the semiconductor laser array elements 10x and 10y, while transmitting the remaining laser beams therethrough, into the collimator unit 2.

The semiconductor laser array elements 10x and 10y respectively have active layers with different compositions which will be described later in this specification, and respectively emit laser beams having a wavelength in a red area and laser beams having a wavelength in an infrared area. The plurality of laser beams LX (red) and the plurality of laser beams LY (infrared) are emitted respectively in phase-locked states. Due to this, output of high power laser light can be realized.

The laser beams LX and LY emitted from the semiconductor laser array elements 10x and 10y are respectively incident on hologram optical elements 2x and 2y in the collimator unit 2.

Each of the hologram optical elements 2x and 2y is designed to collimate incident optical beams that have traveled from light source points at predetermined positions while diverging. Passing through the hologram optical elements 2x and 2y, the laser beams LX and LY become collimated beams. It should be noted here that a collimator lens or the like may instead be used for this purpose.

The reflector unit 3 includes (a) a half mirror 3x for reflecting the laser beams LX that have become collimated beams in the direction of a half mirror 3y and (b) the half mirror 3y for reflecting the laser beams LY that have become collimated beams in the direction of the condenser lens 4. The half mirrors 3x and 3y are well-known optical elements that partially transmit incident optical beams therethrough and reflect the remaining optical beams according to their incidence angles. The half mirrors 3x and 3y are fixed in such a manner that their incidence planes form angles of 45 degrees respectively with chief rays of the laser beams LX and LY.

With this, the laser beams LX reflected by the half mirror 3x pass through the half mirror 3y, and travel in the direction of the condenser lens 4, with being substantially parallel to the laser beams LY reflected by the half mirror 3y. This construction enables the laser beams LX and LY that have been emitted from different positions to travel in the same direction, with their substantial parts being almost overlapped.

The condenser lens 4 condenses incident laser beams LX and LY at predetermined condensing positions on the optical axis. Here, as the incident beams LX and the incident beams LY have different wavelengths, they are condensed at different condensing positions on the optical axis (axial chromatic aberration) as is conventionally known. Accordingly, the laser beams LX and LY respectively form images at different spots SP1 (red) and SP2 (infrared).

To correct such axial chromatic aberration, in the present embodiment, a location of the condenser lens 4 is adjusted in the direction of the optical axis of the condenser lens 4 according to a wavelength of a laser beam for use. This enables stable laser beam machining to be realized, because a location of a beam waist of the laser beam remains the same even when a laser beam with a different wavelength is used. More specifically, the condenser lens is held in a state of being movable in the direction of the optical axis, and the condenser lens driving unit 5 is controlled to drive the condenser lens depending on the wavelength of the laser beam for use, so that laser beams with any wavelength can always be condensed at the same condensing position.

For example, for condensing the two types of laser beams on the spot SP1, the condenser lens 4 is driven along its optical axis by the distance d when the laser beam type is switched from red laser beams to infrared laser beams.

For example, for condensing the two types of laser beams on the spot SP1, the condenser lens 4 is driven along with its optical axis by the distance d when the laser beam type is switched from red laser beams to infrared laser beams.

It should be noted that the condenser lens driving unit 5 may be constructed by a well-known linear actuator that can be controlled finely, such as a screw controller using ball screws. In a case where the condenser lens is composed of a plurality of lenses, at least one lens is moved in the direction of the optical axis to adjust the condensing position.

The control unit 6 not only controls the condenser lens driving unit 5 so as to drive the condenser lens by an appropriate distance, but also controls a laser diode driving unit 7 to drive either one of the semiconductor laser array elements 10x and 10y to emit laser beams. This is explained in detail as follows. The control unit 6 controls the laser diode driving unit 7 to drive one of the semiconductor laser array elements 10x and 10y so as to emit laser beams with a wavelength suitable for usage, according to an operator's indication. Also, the control unit 5 prestores information relating to distances by which the condenser lens 4 is to be driven, in correspondence with a wavelength of laser beams to be emitted from each semiconductor laser array element. Due to this, even when the laser beam type is switched to laser beams with a different wavelength, the laser beams are condensed at the same condensing position. In a case where a stepping motor is employed as a drive source of the condenser lens driving unit 5, the distance by which the condenser lens is driven is easily controlled using its drive pulse.

Figure 2:
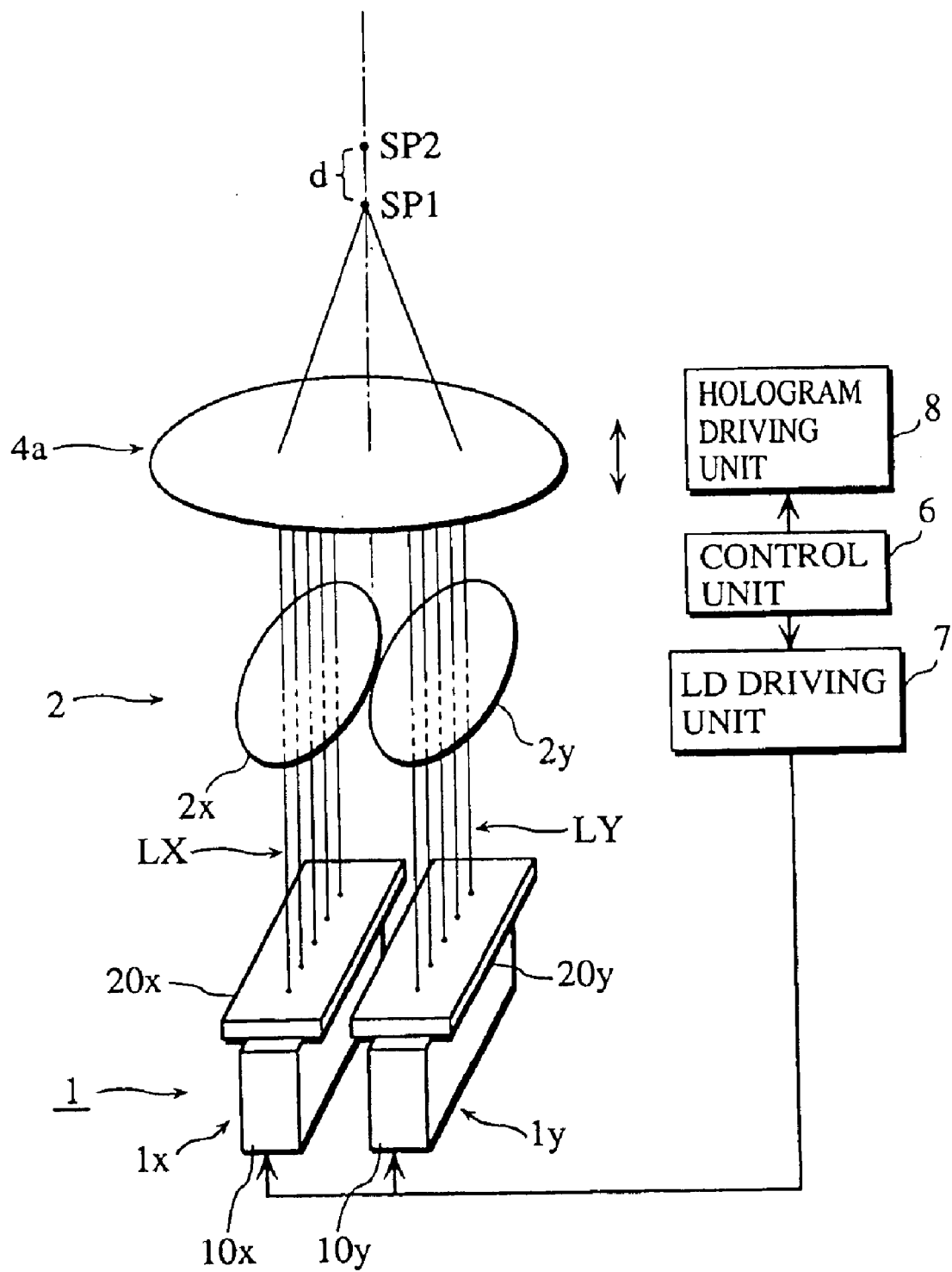
FIG. 2 is a perspective view of an overall construction of another multiple wavelength laser light emitting apparatus relating to the first embodiment of the present invention.

FIG. 2 shows a modification of the multiple wavelength laser light emitting apparatus. This multiple wavelength laser light emitting apparatus in FIG. 2 differs from the one in FIG. 1 in that the reflector unit 3 is not provided, and a hologram optical element 4a that performs a condensing operation on behalf of the condenser lens 4 is provided. Optical distortion is less likely to occur for the hologram optical element 4a compared with the condenser lens even though the hologram optical element with a larger aperture is used. Therefore, by employing the hologram optical element with a large aperture, the half mirror 3 for making the laser beams LA and LB travel on the similar paths becomes unnecessary. The plurality of laser beams LA and the plurality of laser beams LB can travel with a certain space in between and are made directly incident on the hologram optical element 4a. Due to this, the multiple wavelength laser light emitting apparatus can be further downsized. Also, this can reduce a number of components and steps needed for manufacturing, which leads to decreases in the manufacturing cost.

Furthermore, with the construction using the half mirror 3y as shown in FIG. 1, a loss of light is substantial, as the half mirror 3y only partially reflects the laser beams LX and LY while transmitting the remaining light. This modification is free from such a loss of light and is energy-saving.

Here, the axial chromatic aberration also occurs due to a difference of wavelengths of employed laser beams. To condense laser beams with different wavelengths at the same condensing position, it is necessary for the hologram driving unit 8 to drive the hologram optical element 4a, depending on the wavelength of the employed laser beams. This adjustment is not explained here as it is performed in the same manner as the multiple wavelength laser light emitting apparatus shown in FIG. 1.

The semiconductor laser devices 1x and 1y are capable of outputting high power laser beams, the construction of which is described as follows. The size of the semiconductor laser devices 1x and 1y are extremely small, and so an apparatus employing these semiconductor laser devices 1x and 1y can be small in size. Moreover, the semiconductor laser devices 1x and 1y are capable of emitting laser beams with different wavelengths using the same optical system.

(2) Construction of Semiconductor Laser Devices 1x and 1y

Figure 3:
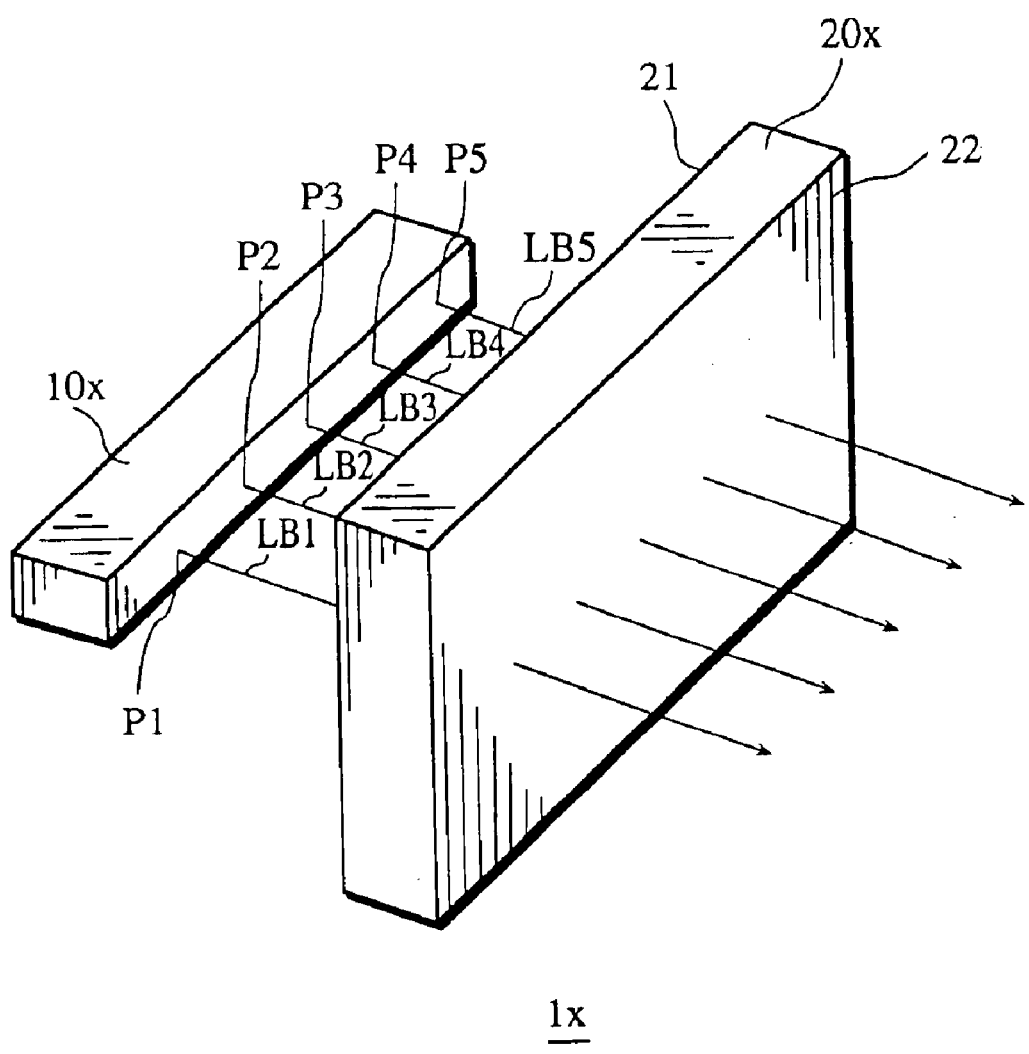
FIG. 3 is a perspective view of an overall construction of a semiconductor laser device relating to the first embodiment of the present invention.

FIG. 3 is a perspective view of an overall construction of the semiconductor laser device 1x relating to the first embodiment of the present invention. It should be noted that the semiconductor laser devices 1x and 1y have the same construction, with the only difference being in the compositions of their semiconductor laser array elements which will be described later. Therefore, the following only explains the semiconductor laser device 1x as one example.

As shown in the figure, the semiconductor laser device 1x is composed of the semiconductor laser array element 10x that emits laser beams LB1 to LB5 respectively from emitting points P1 to P5 thereof (note that each emitting point is a point where a chief ray of each laser beam is emitted from its end face), and the optical element 20x.

Figure 4:
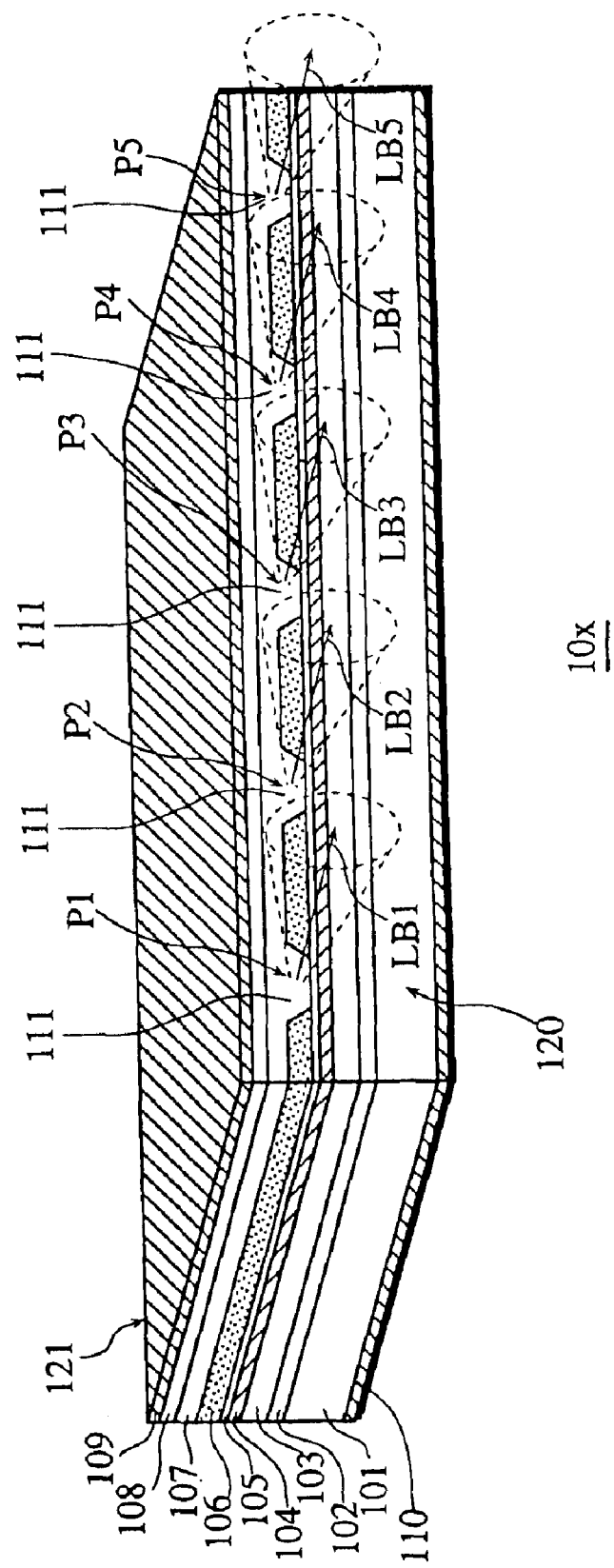
FIG. 4 is a perspective view showing a light source unit of the semiconductor laser device in the first embodiment.

An explanation is first given on the construction of the semiconductor laser array element 10x. FIG. 4 is a perspective view schematically showing the construction of the semiconductor laser array element 10x. In the figure, a solid line indicates a chief ray of each of the laser beams LB1 to LB5, and a broken line indicates a beam width of each of the laser beams LB1 to LB5.

The semiconductor laser array element 10x has the array structure in which five red laser light oscillators each having a real refractive index guided self-aligned structure are arranged parallel to each other. The semiconductor laser array element 10x has an n-type GaAs substrate 101, on which an n-type GaAs buffer layer 102, an n-type AlGaInP cladding layer 103, an GaInP/AlGaInP quantum well active layer 104, a p-type AlGaInP cladding base layer 105, an n-type AlInP current blocking layer 106, a p-type AlGaInP buried cladding layer 107, and a p-type GaAs cap layer 108 (a heat sink) are successively formed in the stated order, and a p-type electrode 109 made by laminating three layers respectively made of Cr, Pt, and Au is formed on the p-type GaAs cap layer 108, and an n-type electrode 110 made by laminating three layers respectively made of AuGe, Ni, and Au is formed on the back of the n-type substrate 101. It should be noted that current channels 111 are formed in stripes in the p-type AlGaInP buried cladding layer 107, in each current channel an electric current supplied from the p-type electrode 109 being narrowed. It should also be noted that the semiconductor laser array element 10y in the semiconductor laser device 1y is different from the semiconductor laser array element 10x only in the composition of some of the layers, where GaAs and GaAlAs are used instead of GaInP and AlGaInP.

The semiconductor laser array element 10x is provided with cleavage planes 120 and 121, which are respectively formed in the direction perpendicular to the lamination direction of the above explained layers, so as to face each other. The cleavage plane 121 has reflectivity of approximately 100%, whereas the cleavage plane 120 has predetermined reflectivity of several % and these cleavage planes 120 and 121 form laser light resonators.

With such a construction, an electric current supplied from the p-type electrode 109 is narrowed while flowing through each current channel 111, causing light-producing oscillation in the GaInP/AlGaInP quantum well active layer formed below. Refractive index of the n-type AlInP current blocking layer 106 is smaller than that of the p-type AlGaInP cladding base layer 105. Due to this difference in the refractive index, laser light is confined within each current channel 111. The laser light confined within each current channel 111 oscillates back and forth at a wavelength determined by the size of each resonator formed between the cleavage planes 120 and 121, and is emitted as the laser beams LB1 to LB5 from the emitting points P1 to P5. As the broken line indicates, a cross section of each of the laser beams LB1 to LB5 is oval-shaped, which has a longer length in the lamination direction. Each of the laser beams LB1 to LB5 diverges, increasing its beam width, as it travels away from each of the emitting points P1 to P5.

The optical element 20x is made from a transparent glass plate, and includes an incidence plane 21 on which the laser beams LB1 to LB5 are incident and an output plane 22 from which the laser beams that have transmitted through the incidence plane 21 are outputted, as shown in FIG. 3.

Figure 5:
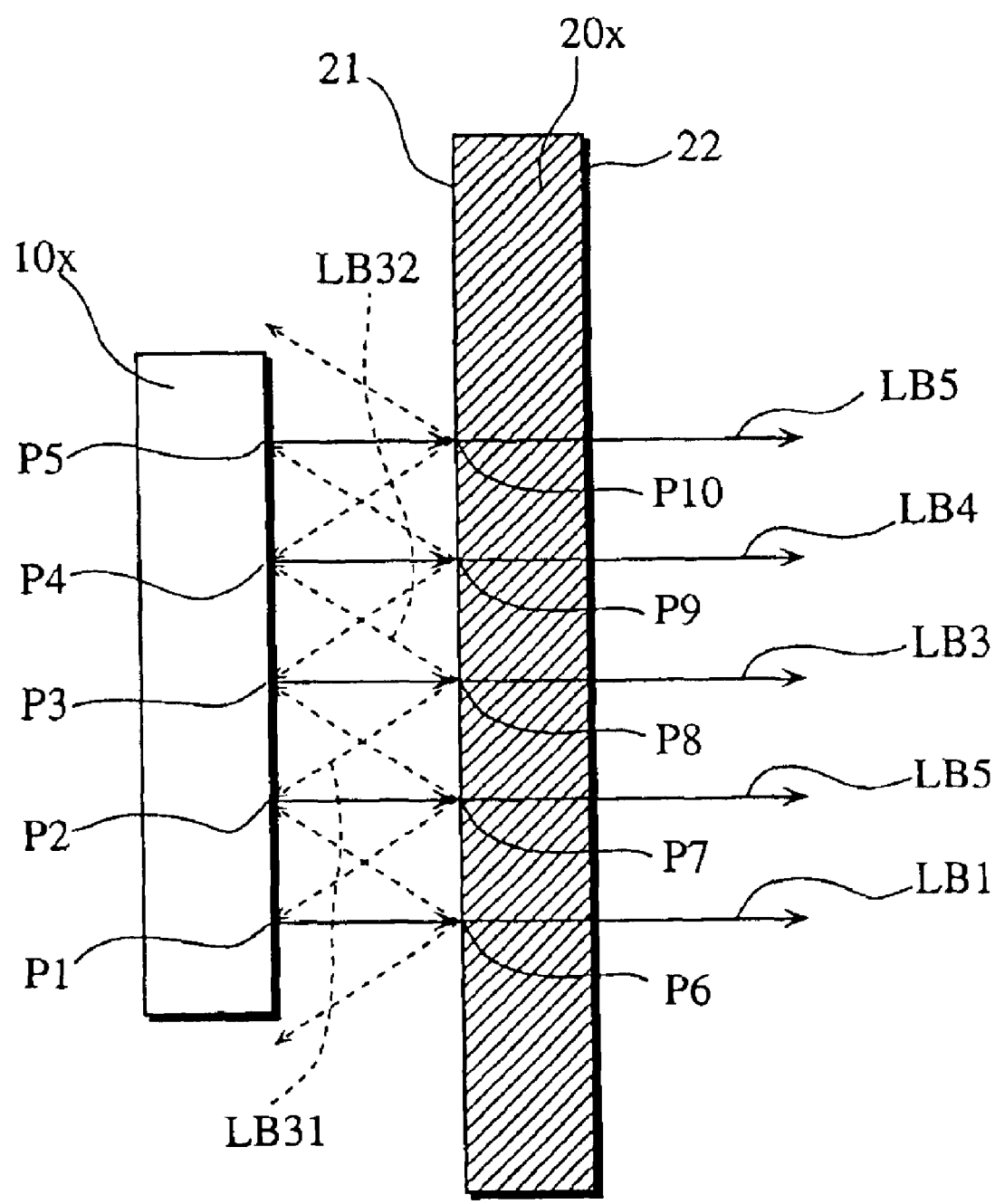
FIG. 5 is a top view of the semiconductor laser device in the first embodiment, showing optical paths of laser beams.

FIG. 5 is a top view of the semiconductor laser device 1x to show the physical relationship between the optical element 20x and the semiconductor laser array element 10x. In the figure, a solid line indicates a chief ray of each of the laser beams LB1 to LB5, and a broken line indicates reflected light.

The optical element 20x made from the transparent glass plate is used for partially reflecting incident laser beams emitted from the emitting points P1 to P5 back to other emitting points P1 to P5. The optical element 20x is fixed with a supportive member (not illustrated) in such a manner that the laser beams LB1 to LB5 are respectively incident on the incidence plane 21 at the emitting points P6 to P10 at approximately right angles. It should be noted here that the distance between the optical element 20x and the semiconductor laser array element 10x is set at least longer than the distance between adjacent two emitting points. This is because the laser beams are not reflected back to the emitting points if the distance between the optical element 20x and the semiconductor laser array element 10x is too short.

It is preferable to set the size of the incidence plane 21 of the optical element 20x large enough to receive all the laser beams emitted from the semiconductor laser array element 10x. As the laser beams emitted form the semiconductor laser array element 10x travel while diverging and increasing their beam widths, the size of the incidence plane 21 is to be determined taking (1) the distance between the optical element 20x and the semiconductor laser array element 10x, and (2) an angle of divergence of each laser beam emitted from the semiconductor laser array element 10x, into consideration.

Also, the surface of the incidence plane 21 is flat, with having been subjected to mirror grinding, and its reflectivity is made approximately in the range of 10% to 30%. Therefore, the laser beams LB1 to LB5 substantially transmit through the incidence plane 21 and are outputted from the output plane 22. On the other hand, the remaining portions of the laser beams LB1 to LB5 are reflected by the incidence plane 21 in accordance with their angles of divergence, and return to emitting points P1 to P5. Here, each laser beam returns to emitting points adjacent to an emitting point from which the laser beam is emitted. If the reflectivity of the incidence plane 21 is too high, the amount of laser beams that transmit through the optical element 20 decreases, and so efforts for realizing output of high power laser light by increasing the amount of laser beams to be condensed are disturbed. On the other hand, if the reflectivity of the incidence plane 21 is too low, the amount of laser beams that return to the emitting points decreases, decreasing a chance of laser beams to be phase-locked (phase-locking is described in detail later). Therefore, it is desirable to set the reflectivity of the incidence plane 21 approximately in the range of 10% to 30%.

Here, for explaining reflection of the laser beams LB1 to LB5 by the incidence plane 21 in more detail, the following takes the laser beam LB3 emitted from the emitting point P3 as one example. The other laser beams LB1, LB2, LB4, and LB5 are not explained as they are reflected in the same way as the laser beam LB3.

As the laser beam LB3 travels while diverging and increasing its beam width, the laser beam LB3 is incident on the incidence plane 21 in a state of diverging. At this point, the laser beam LB3 is partially reflected by the incidence plane 21 according to its angle of divergence, so as to generate reflected beams LB31 and LB32 that are directed to the emitting points P2 and P4 adjacent to the emitting point P3 (reflected beams to the emitting points P1 and P5 are also generated though not illustrated).

The reflected beams LB31 and LB32 partially transmit through the cleavage plane 120 (FIG. 4) at the emitting points P2 and P4 so as to return into resonators formed by the cleavage planes 120 ad 121 (FIG. 4) respectively. Therefore, within each resonator, a laser beam oscillates back and forth, so as to generate a laser beam that resonates with the laser beams LB31 or LB32 in phase and wavelength, that is, with the laser beam LB3 in phase and wavelength, by so called an inducing phenomena. Accordingly, wavelengths and phases of the laser beams LB2 and LB4 respectively emitted from the emitting points P2 and P4 are synchronized with those of the laser beam LB3, that is to say, the laser beams LB2, LB3, and LB4 are phase-locked.

The explanation was given on the laser beam LB3 emitted from the emitting point P3, but the same reflection occurs for other laser beams emitted from other emitting points as indicated with a broken line in FIG. 5. A laser beam emitted from each of the emitting points P1 to P5 is reflected back to emitting points adjacent to an emitting point from which the laser beam has been emitted, as well as to the other emitting points (not illustrated). As a result, all the laser beams LB1 to LB5 are phase-locked.

With the construction described above, even when an interval between adjacent laser light oscillators in a semiconductor laser array element is so large that laser beams emitted from the semiconductor laser array element cannot be phase-locked by energies filtering through the laser light oscillators being combined together, the laser beams are partially reflected back to other emitting points with the use of the such an optical element. Therefore, the laser beams emitted from the emitting points can be phase-locked.

It should be noted here that the surface of the incidence plane 21 may have irregular depressions and protrusions. For example, if the surface of the incidence plane 21 has irregular depressions and protrusions like a ground glass, laser beams are reflected irregularly by this incidence plane 21, increasing the amount of laser beams returning to the emitting points, compared with a case where the surface of the incidence plane 21 is flat and the laser beams only partially return to the emitting points. In the former case, phase-locking of the laser beams is ensured.

Also, it is desirable that each of the laser beams reflected by the optical element is directed particularly to a central part of each of the emitting points P1 to P5 on the cleavage plane 120, that is, in the vicinity of the optical axis of each of the emitted laser beams. By doing so, a phenomena for inducing other laser beams easily occurs, thereby the laser beams are more likely to be phase-locked.

Second Embodiment

A multiple wavelength laser light emitting apparatus in the second embodiment has the same construction as the multiple wavelength laser light emitting apparatus described in the first embodiment, with the only difference being in the form of its semiconductor laser devices. Accordingly, the following explains the semiconductor laser devices in the second embodiment.

In the semiconductor laser device 1x in the first embodiment, the incidence plane 21 of the optical element 20x is flat, however, in the second embodiment, an optical element has a diffraction grating on its incidence plane. A semiconductor laser device that emits red laser beams and a semiconductor laser device that emits infrared laser beams are different only in the compositions of the semiconductor laser array elements as in the first embodiment, and therefore, the following only explains a semiconductor laser device 12x as one example.

Figure 6:
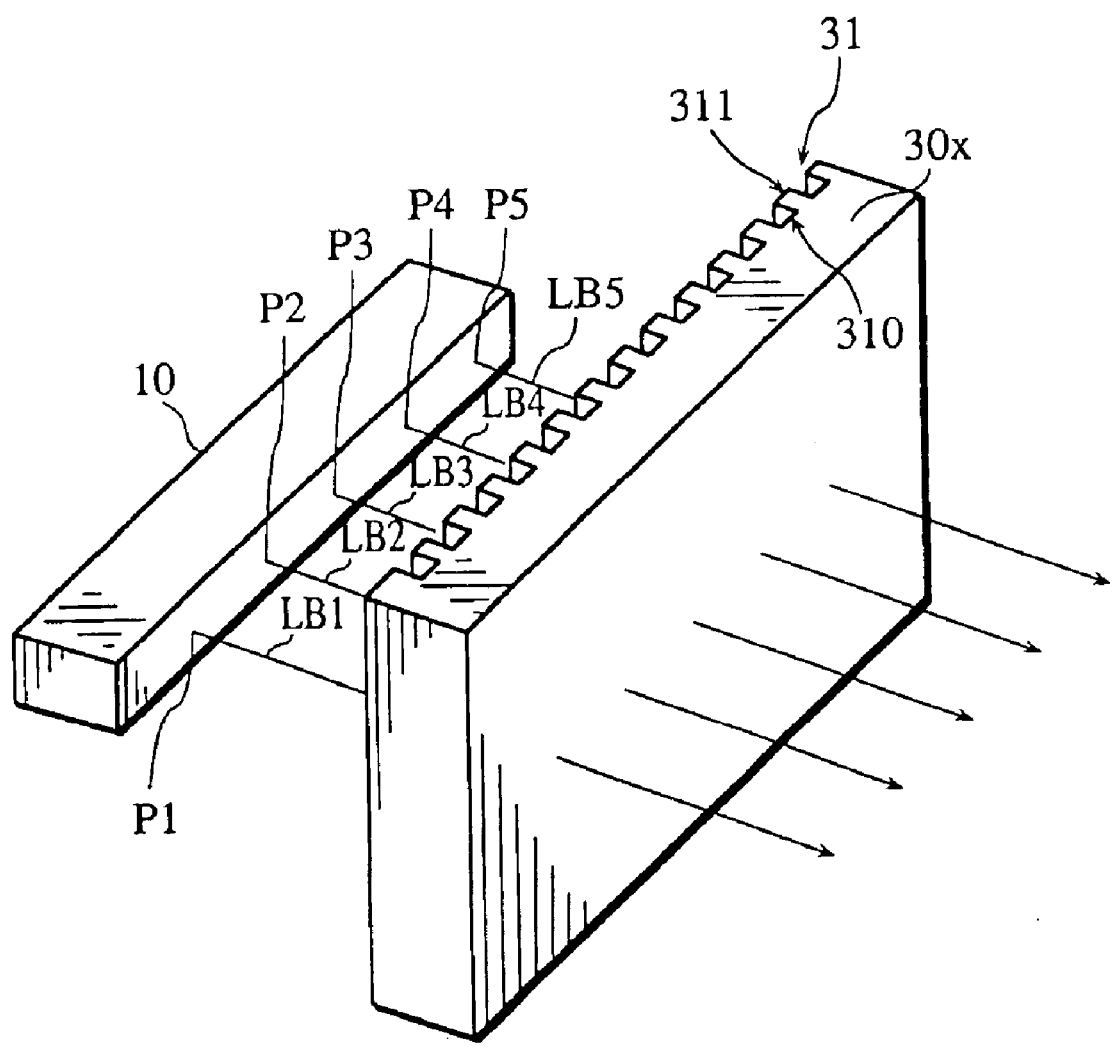
FIG. 6 is a perspective view of an overall construction of a semiconductor laser device relating to a second embodiment of the present invention.

FIG. 6 is a perspective view schematically showing the construction of the semiconductor laser device 12x in the second embodiment. Only the difference from the semiconductor laser device 1x in FIG. 3 lies in the optical element 30x. Elements in FIG. 6 that have the same reference numerals as elements in FIG. 3 are the same as these elements, and therefore are not explained in detail. Also, it should be noted that the diffraction grating in the figure is greatly enlarged for ease of explanation.

The optical element 30x is made from a transparent glass plate, and includes the diffraction grating on the incidence plane 31, the diffraction grating being made by forming grooves in stripes. In more detail, depressions 310 and protrusions 311 are alternately arranged along with the lamination direction of the semiconductor laser array element 10x. The optical element 30x is provided for the same purpose as the optical element 20x in the first embodiment of reflecting laser beams so as to return to other emitting points, with the only difference being its construction for diffracting laser beams in specific directions using the diffraction grating so that the laser beams can return to the other emitting points more efficiently.

Figure 7:
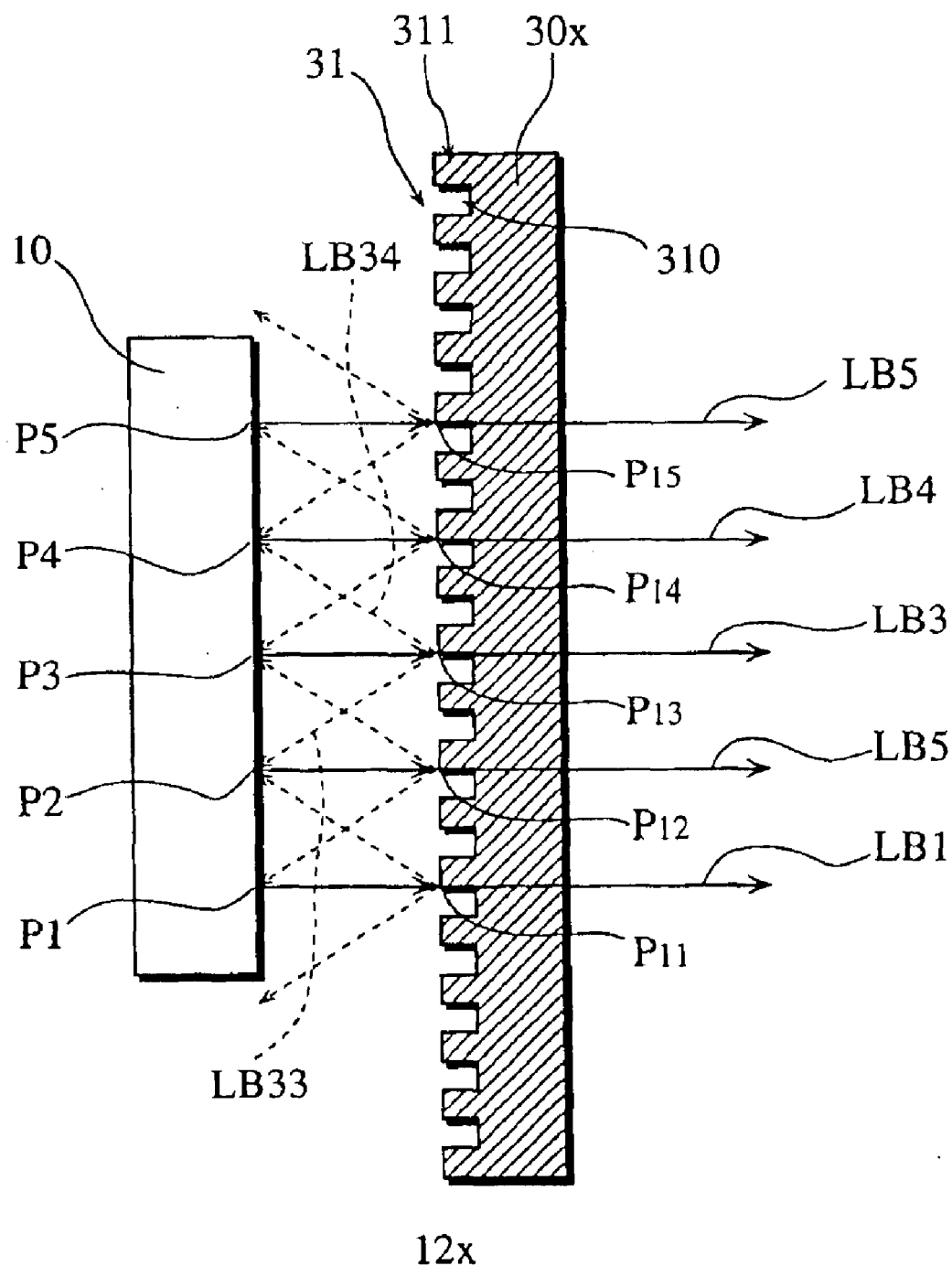
FIG. 7 is a top view of the semiconductor laser device in the second embodiment, showing optical paths of laser beams.

FIG. 7 is a top view of the semiconductor laser device 12x. In the figure, a solid line indicates a chief ray of each of the laser beams LB1 to LB5, and a broken line indicates diffracted light. The diffraction grating is greatly enlarged for ease of explanation.

The optical element 30x is supported by a supportive member (not illustrated) in such a manner that chief rays of the laser beams LB1 to LB5 emitted from the semiconductor laser array element 10x are incident on the incidence plane 31 at right angles. The distance between the optical element 30x and the semiconductor laser array element 10x is predetermined according to diffraction conditions described later.

The following explains diffraction of the laser beam LB3 as one example. The laser beam LB3 is emitted from the emitting point P3 of the semiconductor laser array element 10, and is incident on the incidence plane 31 at the incidence point 13. Here, the laser beam LB3 is partially reflected and diffracted, generating −1st order diffracted light LB33, and +1st order diffracted light LB34 which are respectively directed to the emitting points P2 and P4 adjacent to the emitting point P3.

Figure 8:
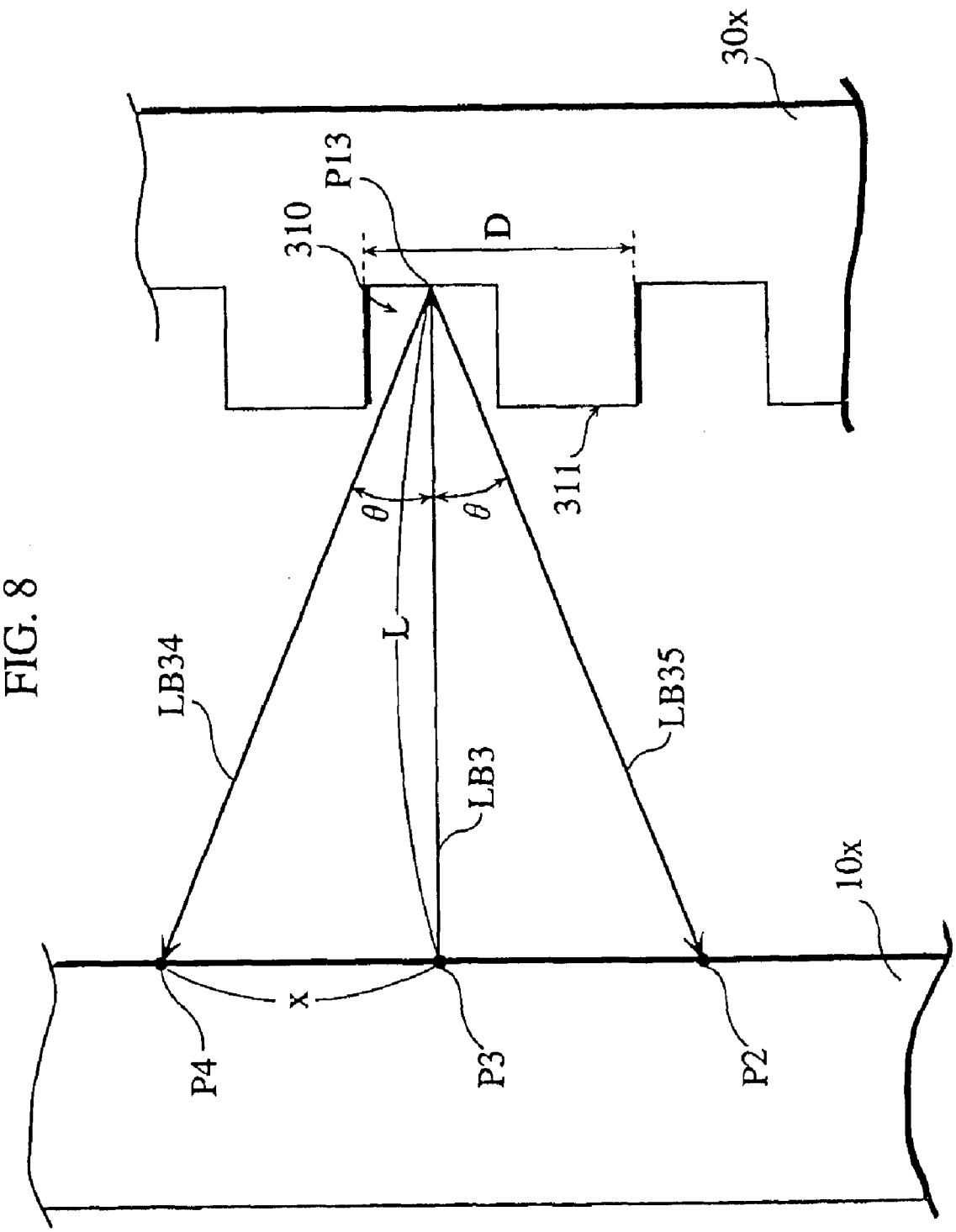
FIG. 8 is the top view of the semiconductor laser device in the second embodiment, showing optical paths of laser beams, partly enlarged to explain diffraction of the laser beams.

FIG. 8 is the top view of the semiconductor laser device 12x showing optical paths of the laser beam LB3 partly enlarged to explain the diffraction conditions. It should be noted that the diffraction grating in the figure is greatly enlarged for ease of explanation.

The diffraction grating is made by forming grooves in stripes, with the depressions 310 and the protrusions 311 being alternately arranged based on a cycle D. The laser beam LB3 that is incident on the incidence plane 31 at the incidence point P13 within the depression 310 is partially diffracted, generating −1st order diffracted light and +1st order diffracted light that are hereafter referred to as a laser beam LB34 and a laser beam LB35 respectively. The laser beam LB34 and the laser beam LB35 are directed at a predetermined diffraction angle θ.

Here, the predetermined diffraction angle θ can be calculated using the following equation 1, assuming that λ is a wavelength of the laser beam LB3.

$$D \sin \theta = \lambda \qquad \text{Equation 1}$$

Also, assuming the distance between the emitting points P3 and P4 (P2) as X, the distance between the emitting point P3 and the incidence plane 312 as L, the diffraction angle θ at which the laser beam LB34 (LB35) is directed to the emitting point P4 (P2) is expressed by the following equation 2.

$$X = L \tan \theta \qquad \text{Equation 2}$$

Using the above equations 1 and 2, the relationship between the distance X and the distance L is expressed as the following equation 3.

$$L = [(D/\lambda)^2 - 1]^{0.5} \cdot X \qquad \text{Equation 3}$$

When the equation 3 is satisfied, the laser beam LB3 emitted from the emitting point P3 is efficiently diffracted at a predetermined diffraction angle back to the emitting points P2 and P4 adjacent to the emitting point P3. In short, if the wavelength λ and the cycle D of depressions and protrusions in the diffraction grating are determined, the distance L can be obtained using the above equation 3, and the optical element 30x is to be placed at a location away from the semiconductor laser device 10x at the obtained distance L. For example, when the conditions is given as "λ=0.65 μm (red laser light), D=2 μm, and X=200 μm", the distance can be obtained as L=582 μm. It should be noted here that a ratio of the width of the protrusion 311 in the cycle D can be any value larger than 0 but lower than 1, but it is desirable to set it at 0.5 where the protrusion 311 and the depression 310 have the same width as the diffraction efficiency of the diffraction grating is the highest in this case.

As described above, by efficiently diffracting the laser beam LB3 back to the emitting points P2 and P4 adjacent to the emitting point P3, the laser beams LB2, LB3, and LB4 respectively emitted from the emitting points P2, P3, and P4 are phase-locked as in the first embodiment. Not only the laser beams LB2, LB3, and LB4 are phase-locked, but also all the laser beams LB1 to LB5 emitted from the emitting points P1 to P5 are phase-locked, as the laser beams LB1 to LB5 are efficiently diffracted back to respective adjacent emitting points as shown in FIG. 7.

With the construction described above, the diffraction grating formed on the incidence plane 31 of the optical element 30x more efficiently diffracts laser beams incident on the incidence plane 31 back to the emitting points, compared with a case in the first embodiment. This enables the laser beams to be phase-locked more efficiently without increasing the reflectivity of the incidence plane.

Third Embodiment

A multiple wavelength laser light emitting apparatus in the third embodiment has the same construction as the multiple wavelength laser light emitting apparatus described in the first embodiment, with the only difference being in the form of its semiconductor laser devices. Accordingly, the following explains the semiconductor laser devices in the third embodiment.

In the semiconductor laser device 1x in the first embodiment, the single semiconductor laser array element is used, however, in the third embodiment, a plurality of semiconductor laser array elements are used in a state of being stacked up.

Figure 9:
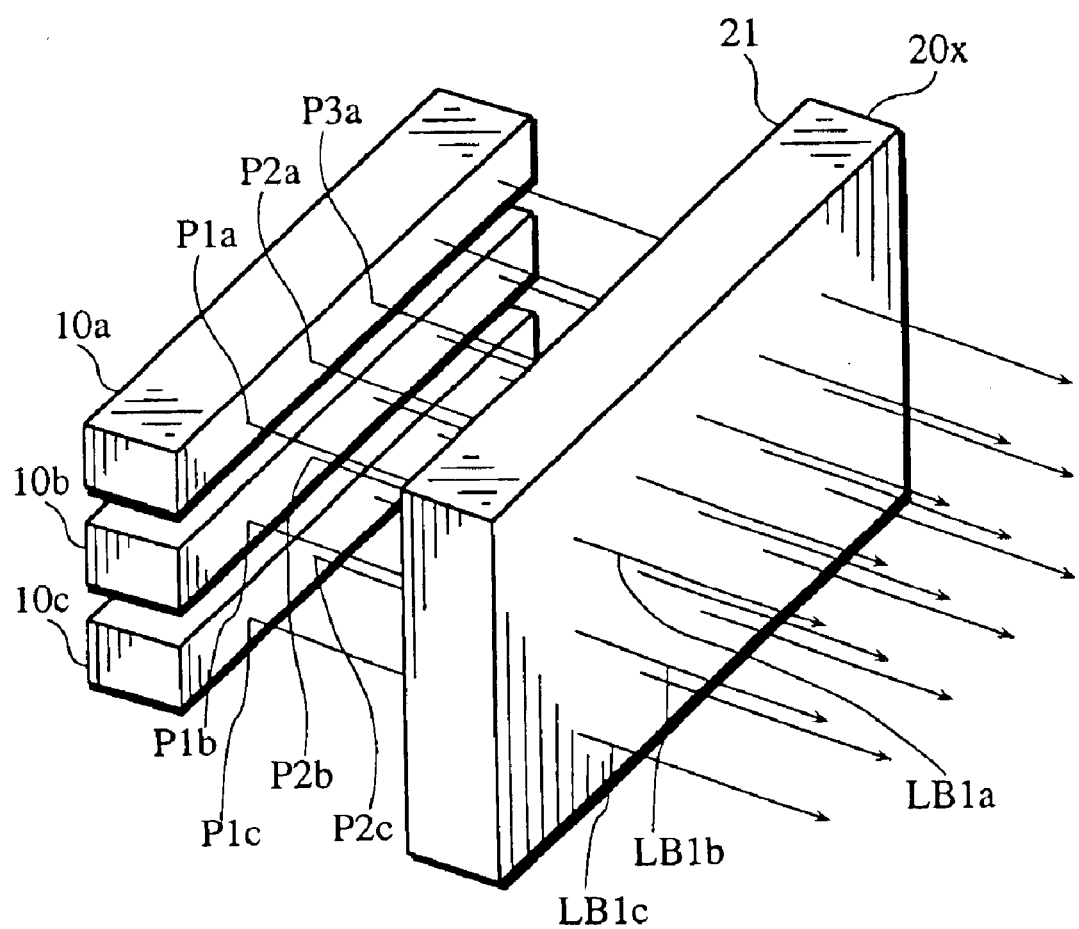
FIG. 9 is a perspective view of an overall construction of a semiconductor laser device relating to a third embodiment of the present invention.

FIG. 9 is a perspective view schematically showing the construction of the semiconductor laser device 13x in the third embodiment. A semiconductor laser device that emits red laser beams and a semiconductor laser device that emits infrared laser beams are different only in the compositions of the semiconductor laser array elements as in the first embodiment, and therefore, the following only explains the semiconductor laser device 13x. Only the difference from the semiconductor laser device 1x in FIG. 3 is that a plurality of semiconductor laser array elements 10a, 10b, and 10c are stacked up in the third embodiment. Elements in FIG. 9 that have the same reference numerals as elements in FIG. 3 are the same as these elements, and therefore are not explained in detail. Also, in the figure, the semiconductor laser array elements 10a, 10b, and 10c are of the same type as the semiconductor laser array element 10x, and the semiconductor laser array elements, the laser beams, and the emitting points are identified with subscripts a, b, and c.

As shown in the figure, emitting points of each of the semiconductor laser array elements 10a, 10b, and 10c are arranged with the same pitch, so that the emitting points of the semiconductor laser array elements 10a, 10b, and 10c are on straight lines in the stack direction of the semiconductor laser array elements 10a, 10b, and 10c (for example, P1a, P1b, P1c are on a straight line).

Each of the semiconductor laser array elements 10a, 10b, and 10c has the same construction as the semiconductor laser array element 1x in the first embodiment. Therefore, due to the diffraction by the optical element 20x, five laser beams emitted from each of the semiconductor laser array elements 10a, 10b, and 10c are phase-locked.

Figure 10:
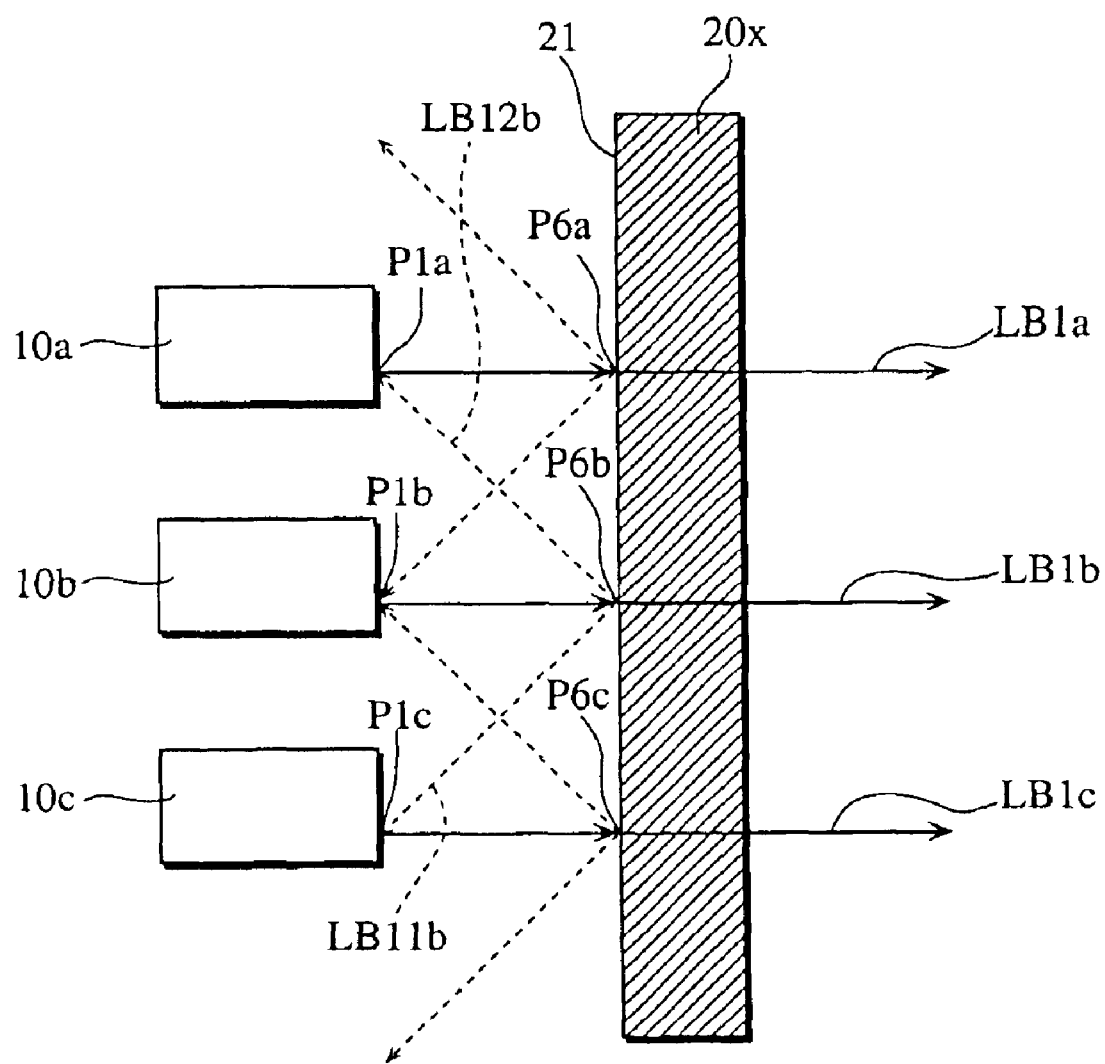
FIG. 10 is a top view of the semiconductor laser device in the third embodiment, showing optical paths of laser beams.

FIG. 10 is a side view of the semiconductor laser device 13x showing optical paths of laser beams. In the figure, a solid line indicates a chief ray of each of the laser beams LB1a to LB1c, and a broken line indicates reflected light.

The laser beams LB1*a* to LB1*c* emitted from the emitting points P1*a* to P1*c* of the semiconductor laser array elements 10*a*, 10*b*, and 10*c* are incident on the incidence plane 21 of the optical element 20*x* at the incidence points P6*a* to P6*c*. Each of the laser beams LB1*a* to LB1*c* is partially reflected by the incidence plane 21.

Here, each laser beam is reflected in the same manner, and so the following explains reflection of the laser beam LB1*b* emitted from the emitting point P1*b* as one example.

As described above, the laser beam LB1*b* travels while diverging and increasing its beam width, and the laser beam LB1*b* is partially incident on the incidence plane 21 at a predetermined incidence angle. The laser beam that has been incident on the incidence plane 21 at the predetermined incidence angle is partially reflected, so as to become reflected light LB11*b* and reflected light LB12*b* which return to the emitting points Pa1 and P1*c* adjacent to the emitting point P1*b* in the stack direction.

Accordingly, the laser beams LB1*a* to LB1*c* emitted from the emitting points P1*a* to P1*c* which are adjacent to each other in the stack direction, each of the emitting points P1*a* to P1*c* belonging to a different semiconductor laser array, are resonated with each other, and phase-locked. Laser beams emitted from different semiconductor laser array elements are phase-locked as described above, and also, laser beams emitted from the same semiconductor laser array element are phase-locked. As a result of this, all the laser beams emitted from the semiconductor laser array elements 10*a*, 10*b*, and 10*c* are phase-locked.

With such a construction, when a plurality of semiconductor laser array elements are used in a state of being stacked up, laser beams emitted from one semiconductor laser array element are reflected back to adjacent emitting points of the semiconductor laser array element and also to adjacent emitting points of other semiconductor laser array elements. This results in laser beams emitted from all the emitting points being phase-locked. Accordingly, phase-locking of laser beams emitted from different semiconductor laser array elements is made possible, which has been impossible with conventional techniques. Therefore, by increasing a number of laser beams and making the laser beams phase-locked, output of high power laser light can be realized.

It should be noted here, when a plurality of semiconductor laser array elements are used in a state of being stacked up as described above, it is desirable that n-type GaAs substrates (the n-type GaAs substrate 101 in FIG. 4), that have been cut out of the same semiconductor wafer are used in the semiconductor laser array elements. As wavelengths of laser beams to be emitted are determined by characteristics of the employed semiconductor wafer, n-type GaAs substrates cut out of different semiconductor wafers may have different characteristics depending on the manufacturing conditions. In this case, wavelengths of laser beams emitted from such semiconductor laser array elements may turn out to be slightly different from each other. On the other hand, when the n-type GaAs substrates cut out of the same semiconductor wafer are used, wavelengths of laser beams emitted from the semiconductor laser array elements are the same, and therefore, only phases of the laser beams should be synchronized, requiring only a small amount of laser light.

Fourth Embodiment

A multiple wavelength laser light emitting apparatus in the fourth embodiment has the same construction as the multiple wavelength laser light emitting apparatus described in the third embodiment, with the only difference being in the form of its semiconductor laser devices. Accordingly, the following explains the semiconductor laser devices in the fourth embodiment.

A semiconductor laser device that emits red laser beams and a semiconductor laser device that emits infrared laser beams are different only in the compositions of the semiconductor laser array elements as in the first embodiment, and therefore, the following only explains the semiconductor laser device 14*x* that emits red laser beams.

In the semiconductor laser device 13*x* in the third embodiment, the incidence plane 21 of the optical element 20*x* is flat, however, in the fourth embodiment, an optical element has a diffraction grating on its incidence plane as in the semiconductor laser device 12*x* in the second embodiment (note that diffraction directions are different).

Figure 11:
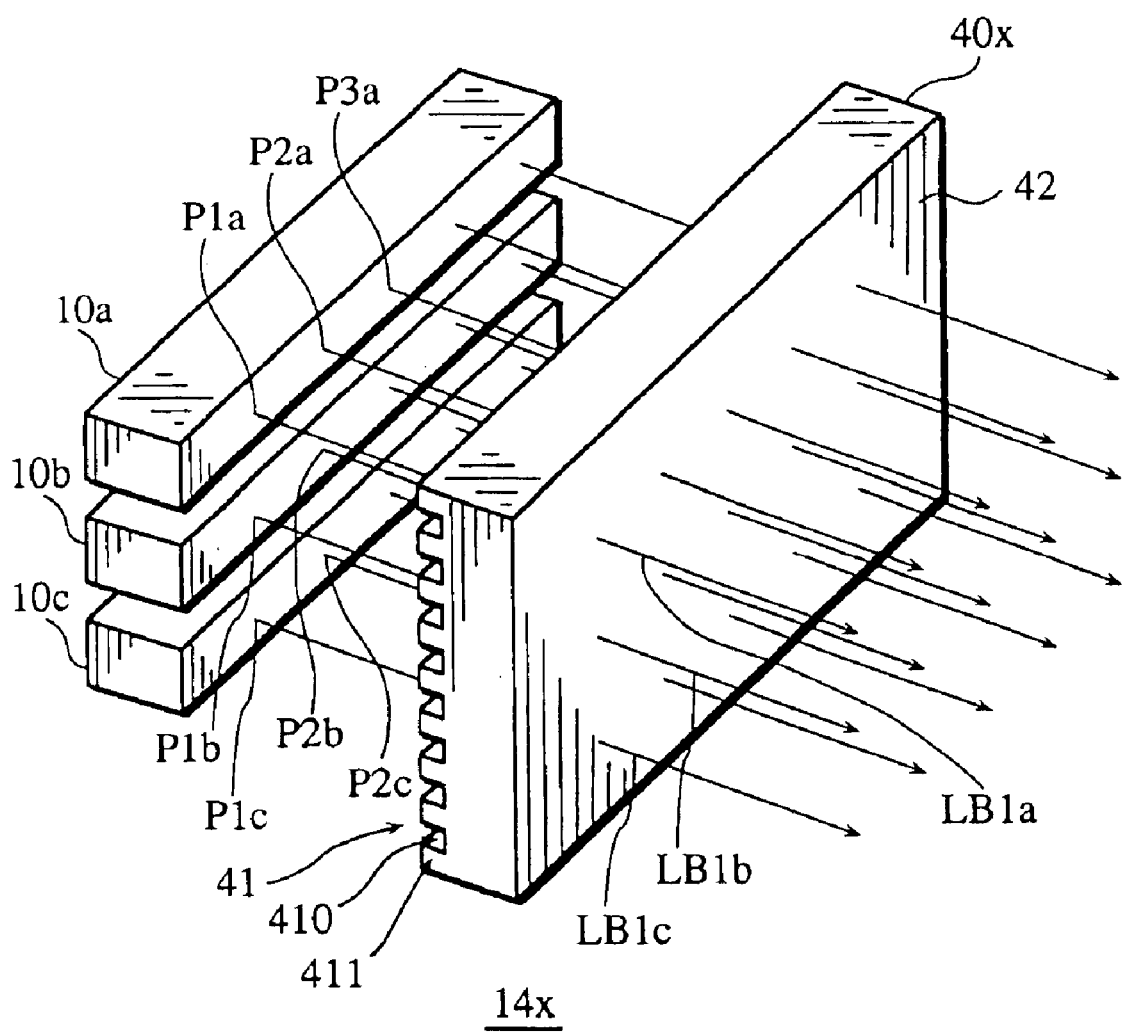
FIG. 11 is a perspective view of an overall construction of a semiconductor laser device relating to a fourth embodiment of the present invention.

FIG. 11 is a perspective view schematically showing the construction of the semiconductor laser device 14*x* in the fourth embodiment. Only the difference from the semiconductor laser device 13*x* in FIG. 9 lies in the optical element 40*x*. Elements in FIG. 11 that have the same reference numerals as elements in FIG. 9 are the same as these elements, and therefore are not explained here.

Figure 12:
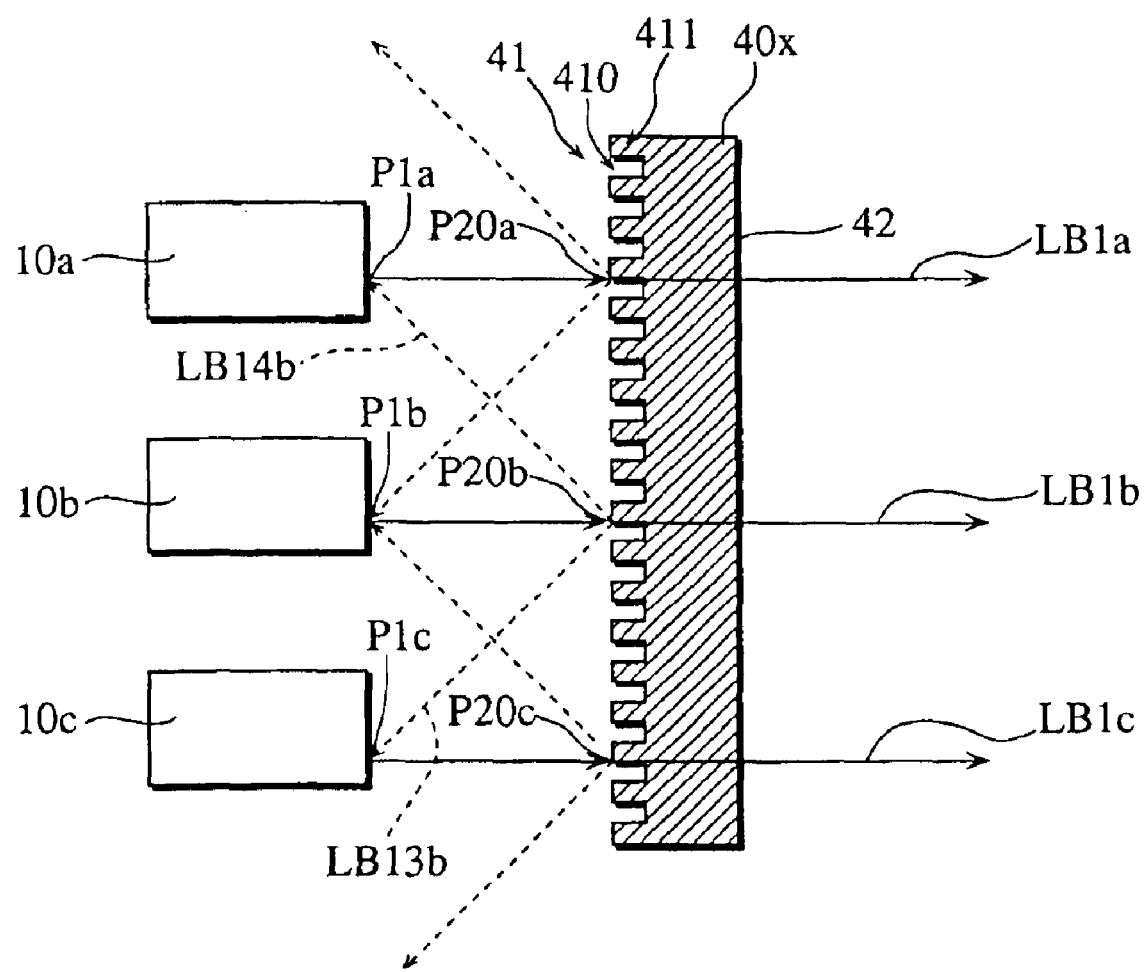
FIG. 12 is a top view of the semiconductor laser device in the fourth embodiment, showing optical paths of laser beams.

The optical element 40*x* includes the diffraction grating on its incidence plane 41, the diffraction grating made by forming grooves in stripes. In more detail, depressions 410 and protrusions 411 are alternately arranged along with a direction perpendicular to the lamination direction of the semiconductor laser array elements 10*a*, 10*b*, and 10*c*. The diffraction grating diffracts incident laser beams in the lamination direction. On the other hand, the laser beams are not diffracted but reflected in the direction perpendicular to the lamination direction. Due to this, five laser beams emitted from each of the semiconductor laser array elements 10*a*, 10*b*, and 10*c* return to emitting points of the semiconductor laser array elements because of a surface reflection of the optical element 40*x*, and are phase-locked as in the first embodiment. Here, each laser beam is diffracted back to emitting points adjacent to a point from which the laser beam is emitted. FIG. 12 is a side view of the semiconductor laser device 14*x* showing optical paths of laser beams. In the figure, a solid line indicates a chief ray of each of the laser beams LB1*a* to LB1*c*, and a broken line indicates minus/+ 1st order diffracted light. As each emitted laser beam travels in the same manner, the following only explains the laser beams LB1*a*, LB1*b*, and LB1*c* respectively emitted form the emitting points P1*a*, P1*b*, and P1*c* as examples.

The laser beams LB1*a*, LB1*b*, and LB1*c* are incident on the incidence plane 41 of the optical element 40*x*. The incident laser beams LB1*a*, LB1*b*, and LB1*c* substantially transmit through the incidence plane 41, and are outputted from the output plane 42, but at the same time, the incident laser beams LB1*a*, LB1*b*, and LB1*c* are partially reflected by the incidence plane 41 at the incidence points P20*a*, P20*b*, and P20*c* where the diffraction grating is formed, generating diffracted light traveling in the stack direction of the semiconductor laser array elements.

Here, the following explains the diffraction of the laser beam LB1*b* emitted from the emitting point P1*b* of the semiconductor laser array element 10*b* as one example. The laser beam LB1*b* is partially diffracted, generating −1st order diffracted light, and +1st order diffracted light which are hereafter referred to as a laser beam LB13*b* and a laser beam LB14*b* respectively.

Figure 13:
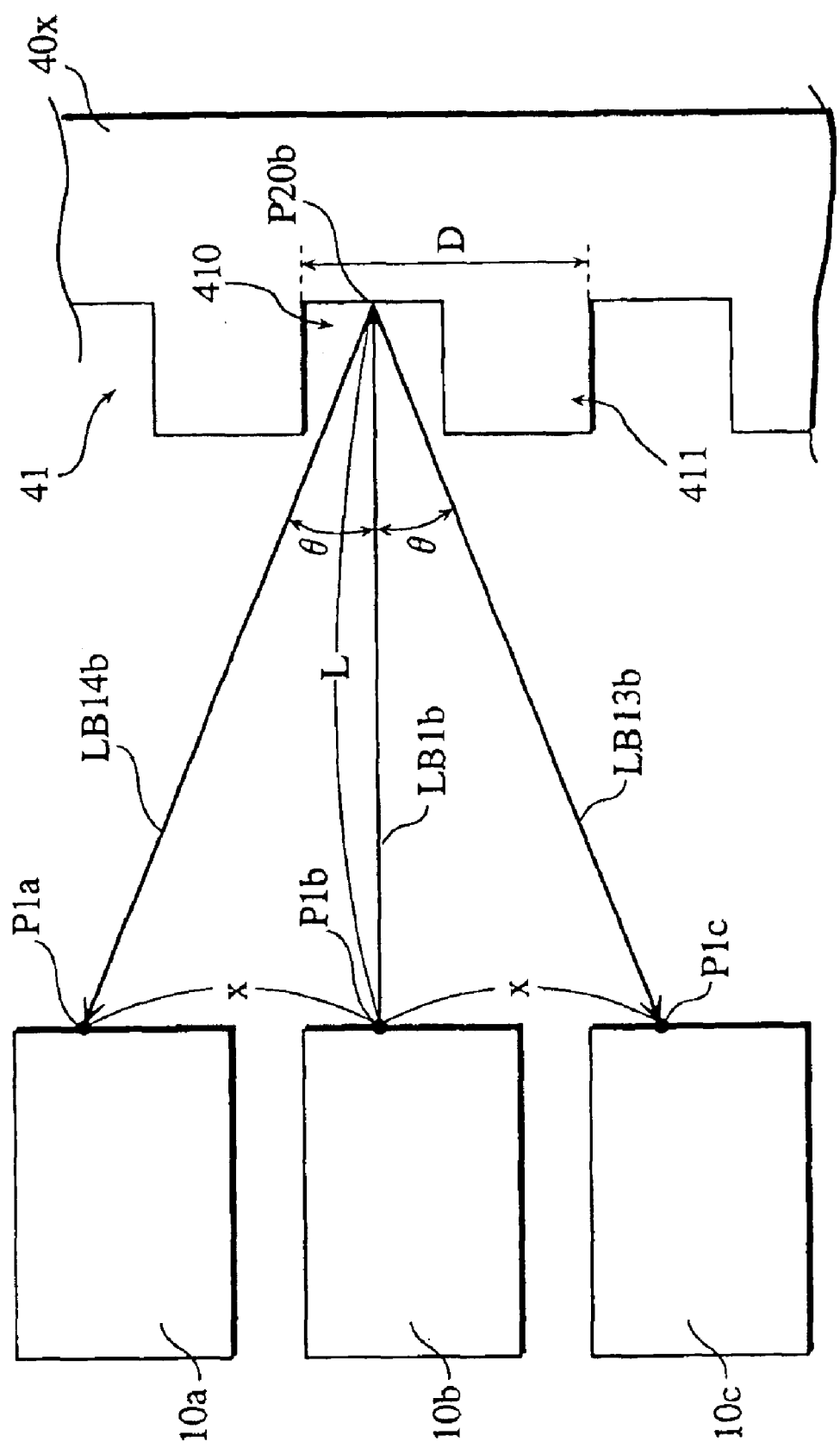
FIG. 13 is the top view of the semiconductor laser device in the fourth embodiment, showing optical paths of laser beams, partly enlarged to explain diffraction of the laser beams.

FIG. 13 is the side view of the semiconductor laser device 14*x* showing optical paths of the laser beam LB1*b*, enlarged to explain its reflection state. It should be noted that the diffraction grating is greatly enlarged in the figure for ease of explanation.

As shown in the figure, when the laser beam LB1*b* emitted from the emitting point P1*b* of the semiconductor laser array element 10*b* is incident on the incidence plane 41 at the incidence point P20*b* within the depression 410 of the diffraction grating, the laser beam LB1*b* is partially diffracted, generating the laser beams LB13*b* and LB14*b* that are respectively directed to the emitting points P1*c* and P1*a* at a predetermined diffraction angle θ. Here, conditions for diffraction, such as the distance Las shown in the figure, can be determined using the equation 3 described in the second embodiment, so that the laser beams LB13*b* and LB14*b* are effectively directed to the points P1*c* and P1*a* at the predetermined diffraction angle. Here, a laser beam emitted from each emitting point is diffracted back to emitting points adjacent to an emitting point in the stack direction, the emitting point from which the laser beam is emitted.

Accordingly, all the laser beams emitted from the semiconductor laser array elements 10*a*, 10*b* and 10*c* can be resonated with each other and phase-locked as in the third embodiment. Moreover, the presence of the diffraction grating enables laser beams to be diffracted back to emitting points of different semiconductor laser array elements, the emitting points adjacent to emitting points in the stack direction from which the laser beams are emitted. Due to this, phase-locking of the laser beams can further be ensured.

Figure 14:
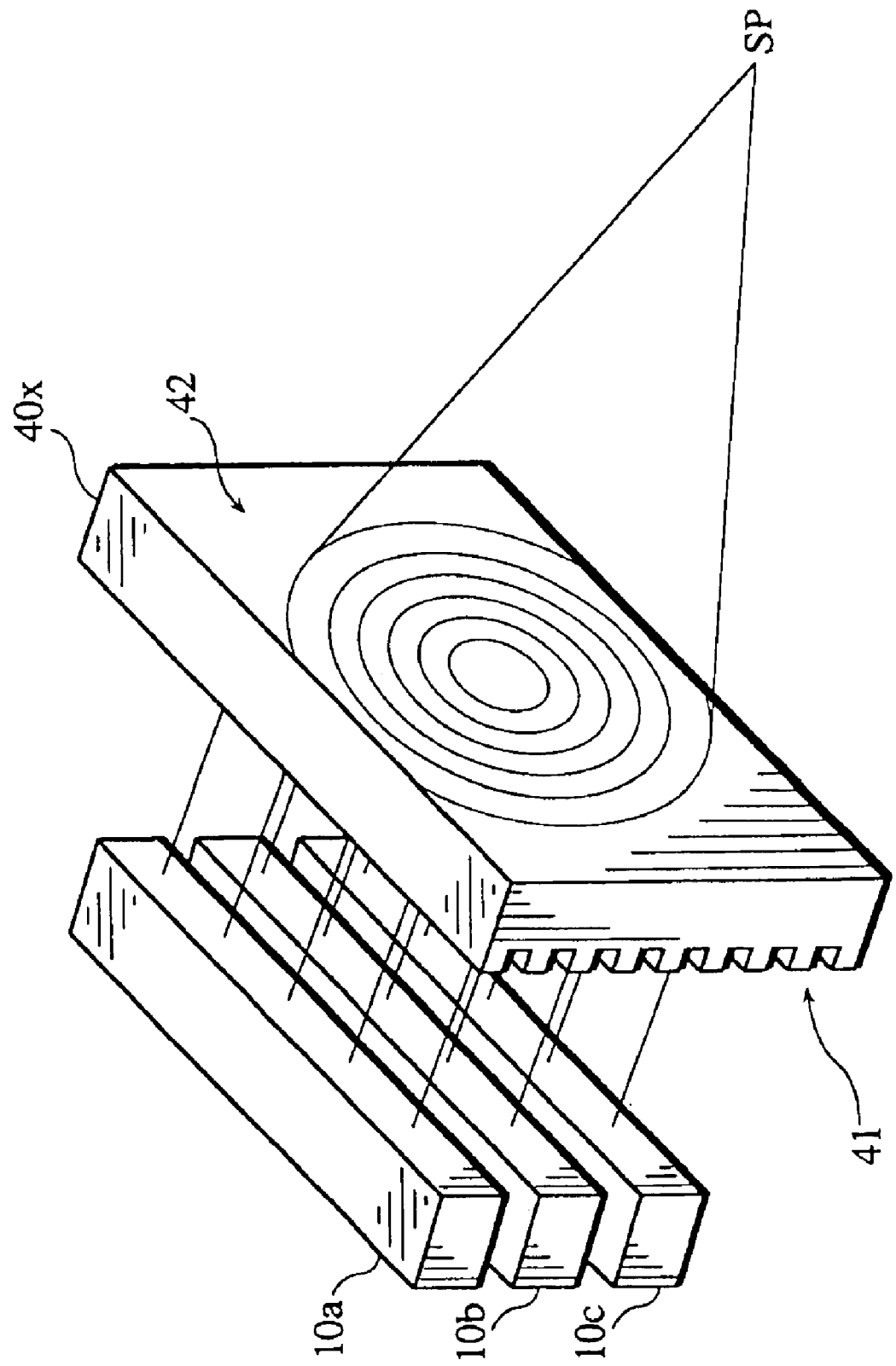
FIG. 14 is a perspective view of an overall construction of a semiconductor laser device relating to a modification in the fourth embodiment of the present invention.

It should be noted that the output plane 42 of the optical element 40*x* may be subjected to hologram processing to make the optical element 40*x* function as a hologram. For example, by subjecting the output plane 42 of the optical element 40*x* of the semiconductor laser device to the hologram processing as shown in FIG. 14, laser beams that have passed through the optical element 40*x* can be directly condensed on the spot SP. Alternatively, the output plane 42 may be subjected to hologram processing that enables the output plane 42 to collimate laser beams, so that the laser beams that have passed through the optical element 40*x* become collimated beams. Employing these, optical elements required for condensing laser beams and collimating laser beams become unnecessary, decreasing a number of optical elements, thereby realizing a semiconductor laser device that is compact and capable of condensing light.

Fifth Embodiment

A multiple wavelength laser light emitting apparatus in the fifth embodiment has the same construction as the multiple wavelength laser light emitting apparatus described in the fourth embodiment, with the only difference being in the form of its semiconductor laser devices. Accordingly, the following explains the semiconductor laser devices in the fifth embodiment.

A semiconductor laser device that emits red laser beams and a semiconductor laser device that emits infrared laser beams are different only in the compositions of the semiconductor laser array elements, and therefore, the following only explains the semiconductor laser device 15*x* that emits red laser beams.

In the second and fourth embodiments, the diffraction gratings diffract incident laser beams respectively in the lamination direction and in the direction perpendicular to the lamination direction, however, the diffraction grating in the fifth embodiment diffracts incident laser beams in both the lamination direction and the direction perpendicular to the lamination direction. This further enhances diffraction performances.

Figure 15:
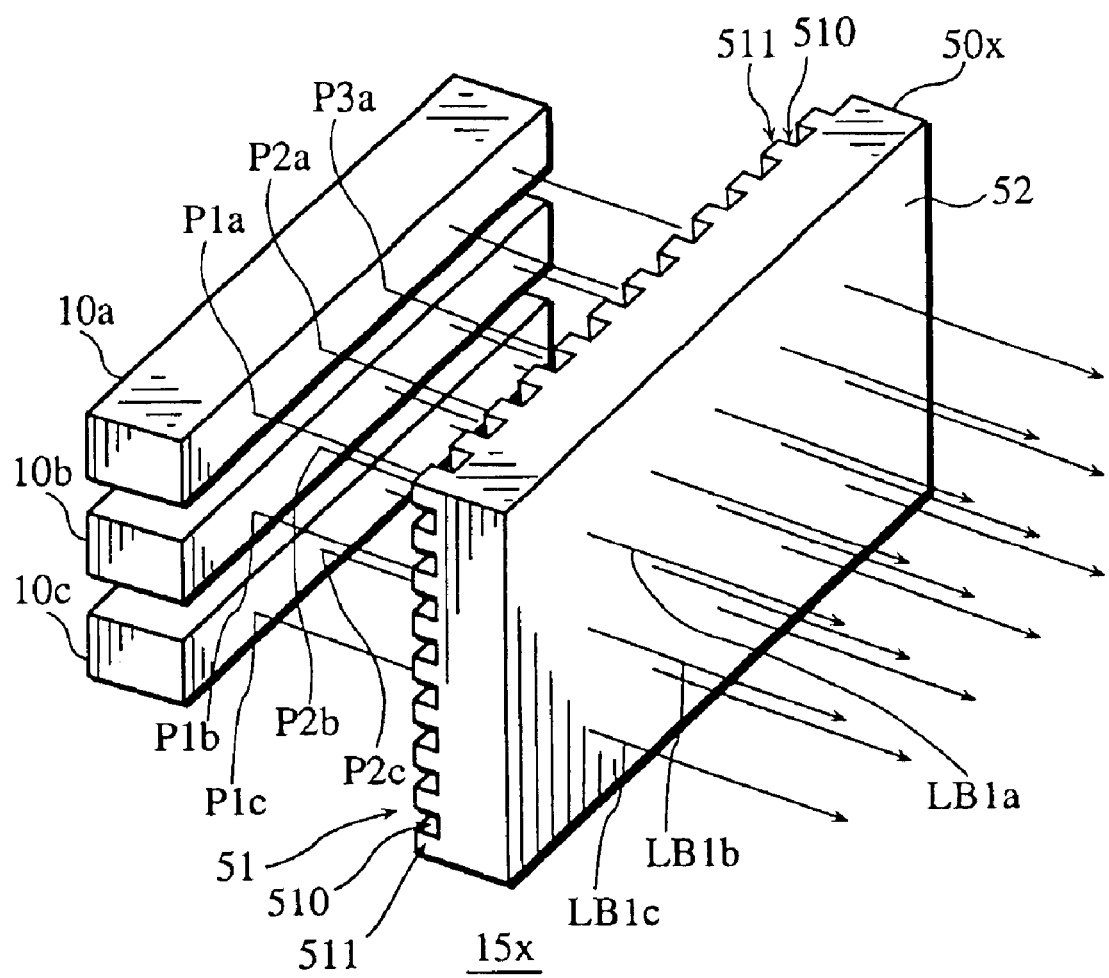
FIG. 15 is a perspective view of an overall construction of a semiconductor laser device relating to a fifth embodiment of the present invention.

FIG. 15 is a perspective view schematically showing the construction of the semiconductor laser device 15*x* in the fifth embodiment. Only the difference from the semiconductor laser device 14*x* in FIG. 11 lies in the optical element 50*x*. Elements in FIG. 15 that have the same reference numerals as elements in FIG. 11 are the same as theses elements, and therefore are not explained here.

The optical element 50*x* includes the diffraction grating on its incidence plane 51 on which laser beams are incident.

Figure 16:
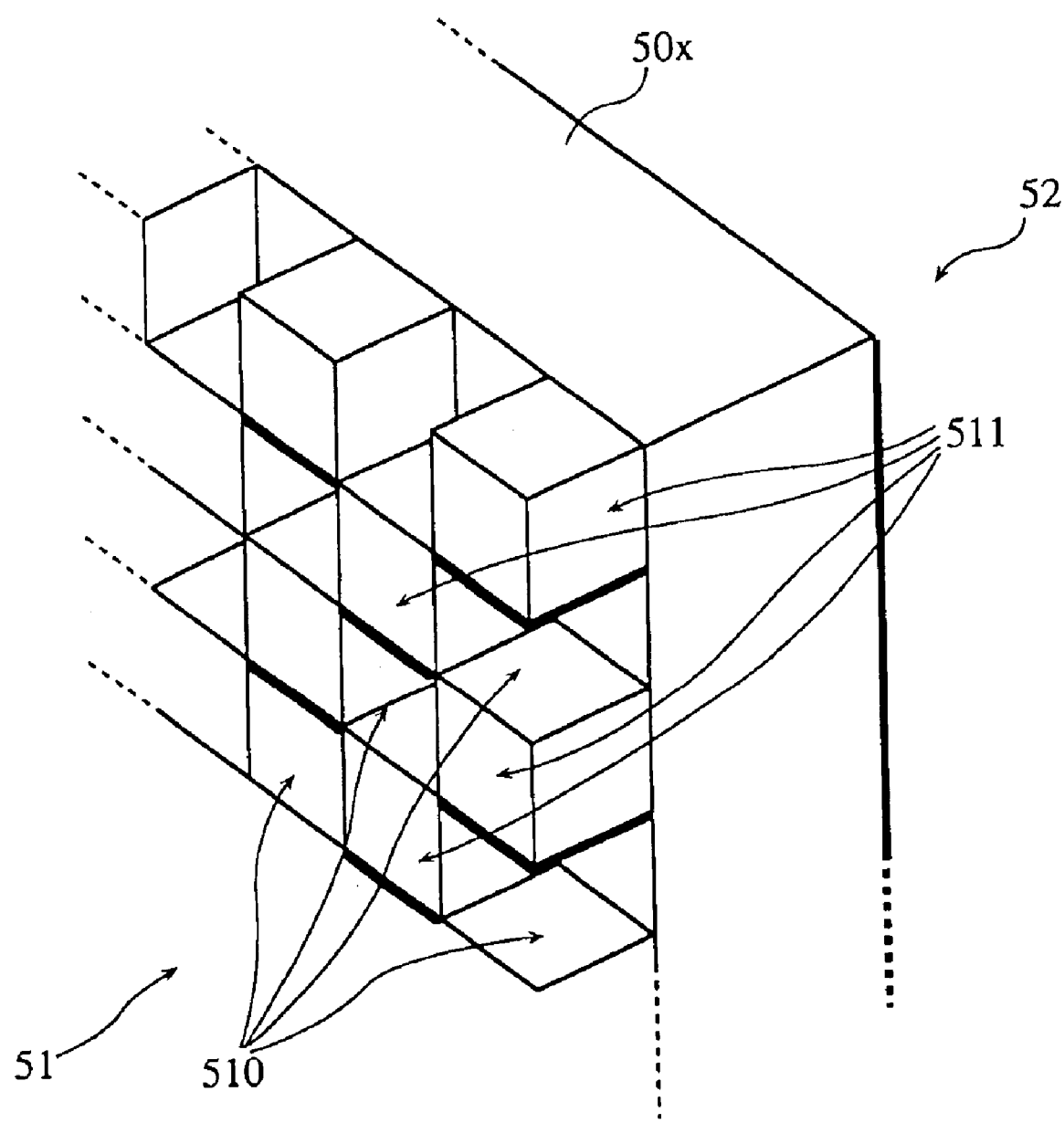
FIG. 16 is a partly enlarged view of an optical element shown in FIG. 15.

FIG. 16 is an enlarged perspective view schematically showing the construction of the incidence plane 51 in the optical element 50*x*.

As shown in the figure, the diffraction grating is made by arranging depressions 510 and protrusions 511 alternately in a stack direction of the semiconductor laser array elements 10*a*, 10*b*, and 10*c* and in a direction perpendicular to the stack direction, to form a checkered pattern as looked at from a direction perpendicular to the incidence plane 51. The diffraction grating partially diffracts incident laser beams in both the stack direction and the direction perpendicular to the stack direction.

With this diffraction grating, five laser beams emitted from each of the semiconductor laser array elements 10*a*, 10*b*, and 10*c* are partially diffracted by the optical element 50*x* back to adjacent emitting points of the semiconductor laser array elements as in the second embodiment, and at the same time, the five laser beams are also diffracted back to adjacent emitting points in the stack direction, that is to say, to adjacent emitting points of different semiconductor laser array elements as in the fourth embodiment. Accordingly, not only laser beams emitted from the same semiconductor laser array elements, but also laser beam emitted from different semiconductor laser array elements are phase-locked. It should be noted here that conditions for the diffractions mentioned in the second and fourth embodiments should be satisfied.

Accordingly, all the laser beams emitted from the semiconductor laser array elements 10*a*, 10*b* and 10*c* can be resonated with each other and are phase-locked as in the fourth embodiment. Moreover, the presence of the diffraction grating in the optical element 50*x* efficiently makes laser beams emitted from each of the semiconductor laser array elements 10*a*, 10*b*, and 10*c* be diffracted back to emitting points of different semiconductor laser array elements adjacent in the stack direction, as well as adjacent emitting points of the semiconductor laser array element, which further ensures phase-locking of all the laser beams.

It should be noted that the output plane 52 of the optical element 50*x* may be subjected to the hologram processing as in the fourth embodiment. By doing so, laser beams that have passed through the optical element 50*x* can be directly condensed on the spot SP. Also, if the output plane is subjected to the hologram processing that enables the output plane 52 to collimate laser beams, the laser beams that have passed through the optical element 50*x* become collimated beams. Employing these, optical elements required for condensing laser beams and collimating laser beams become unnecessary, decreasing a number of optical elements, thereby realizing a semiconductor laser device that is compact and capable of condensing light.

Sixth Embodiment

A multiple wavelength laser light emitting apparatus in the sixth embodiment has the same construction as the multiple wavelength laser light emitting apparatus described in the fourth embodiment, with the only difference being in the form of its semiconductor laser devices. Accordingly, the following explains the semiconductor laser device 16*x* in the sixth embodiment.

A semiconductor laser device that emits red laser beams and a semiconductor laser device that emits infrared laser beams are different only in the compositions of the semiconductor laser array elements 11a, 11b, and 11c, and therefore, the following only explains the semiconductor laser device 16x that emits red laser beams.

In the fourth embodiment, each semiconductor laser array element emits laser beams from end faces on one main surface thereof, however, each semiconductor laser array element in the sixth embodiment emits laser beams not only from the end faces on the one main surface but also from the other main surface thereof. An optical element is provided so as to face the other main surface of the semiconductor laser array elements.

Figure 17:
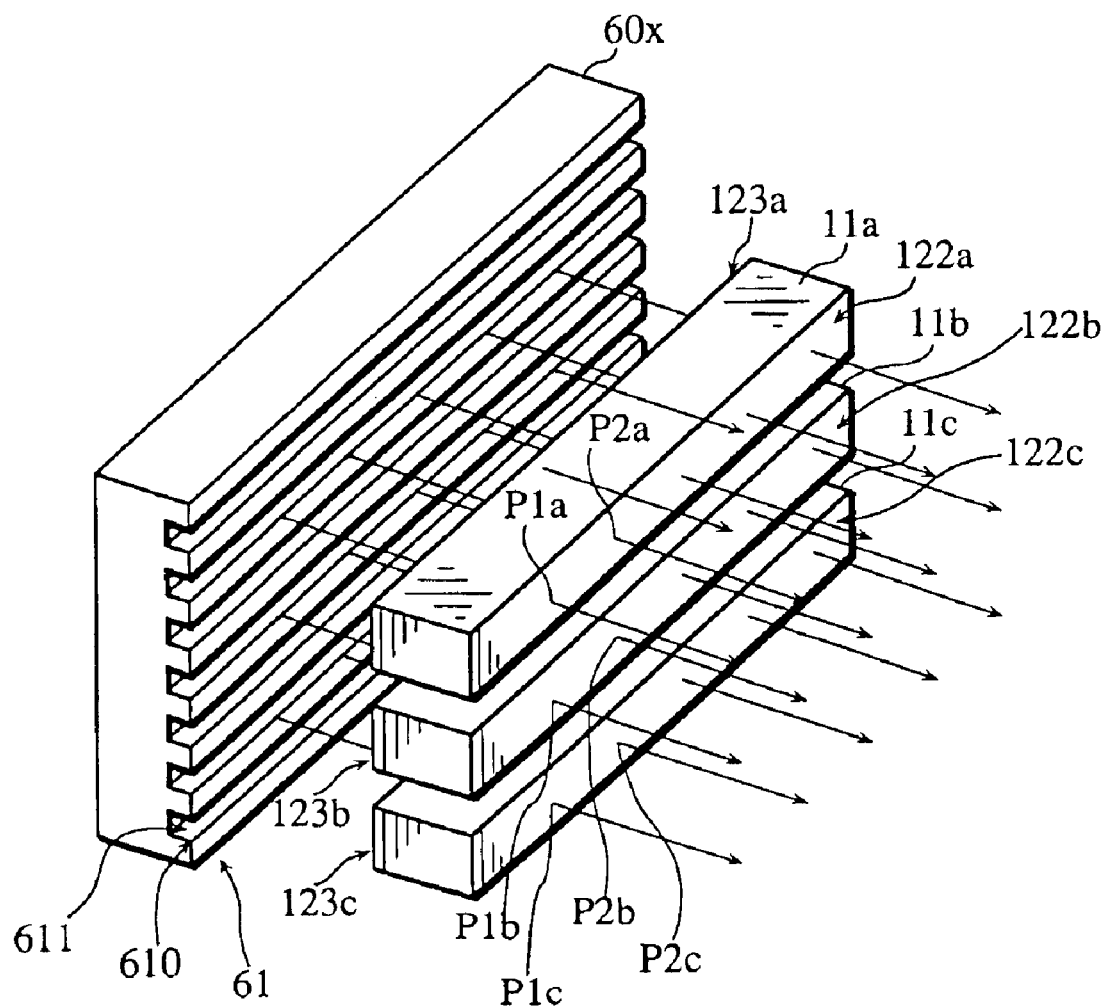
FIG. 17 is a perspective view of an overall construction of a semiconductor laser device relating to a sixth embodiment of the present invention.

FIG. 17 is a perspective view schematically showing the construction of the semiconductor laser device 16x in the sixth embodiment. Only the difference from the semiconductor laser device 14x in FIG. 11 is the location of the optical element 60x and that the semiconductor laser array elements 11a, 11b, and 11c emit laser beams from both the cleavage planes. The present embodiment is explained focusing on these differences.

As shown in the figure, the semiconductor laser device 16x is composed of the semiconductor laser array elements 11a, 11b, and 11c, and the optical element 60x.

The semiconductor laser array elements 11a, 11b, and 11c have approximately the same construction as the semiconductor laser array element 1x described in the first embodiment, with the only difference being that the cleavage planes 123a, 123b, and 123c having reflectivity of less than 100%. Laser beams are emitted from emitting points P1a to P5c on the cleavage planes 122a, 122b, and 122c, whereas laser beams are also emitted from emitting points (not illustrated) on the cleavage planes 123a, 123b, and 123c.

The optical element 60x includes a diffraction grating on its incidence plane 61 on which laser beams emitted from the cleavage planes 123a, 123b, and 123c are incident. Locations where the optical element 60x and the semiconductor laser array elements 11a, 11b, and 11c are disposed and a form of the diffraction grating should be determined so as to meet the same conditions as in the fourth embodiment. The diffraction grating is made by forming grooves in stripes, with depressions 610 and protrusions 611 being alternately arranged along with a direction perpendicular to the lamination direction of the semiconductor laser array elements 11a, 11b, and 11c. The diffraction grating diffracts incident laser beams in the lamination direction. On the other hand, the laser beams are not diffracted but reflected in the direction perpendicular to the lamination direction.

Therefore, five laser beams emitted from each of the semiconductor laser array elements 11a, 11b, and 11c are diffracted back to adjacent emitting points in the stack direction due to a surface reflection on the incidence plane 61 of the optical element 60x, that is to say, to adjacent emitting points of different semiconductor laser array elements as in the fourth embodiment, and at the same time, the diffraction grating 60x diffracts the five laser beams back to adjacent emitting points in the lamination direction, the adjacent emitting points belonging to different semiconductor laser array elements. Accordingly, not only laser beams emitted from the same semiconductor laser device, but also laser beams emitted from different semiconductor laser devices are phase-locked. This enables the semiconductor laser device to output higher power laser light.

Here, laser beams can be more efficiently diffracted back if the diffraction grating described in the fifth embodiment is formed on the incidence plane 61 of the optical element 60x, the diffraction grating reflecting and diffracting incident laser beams in the lamination direction or in the direction perpendicular to the lamination direction. In this case, laser beams can be phase-locked more easily.

Also, the incidence plane 61 of the optical element 60x may be subjected to a well-known high reflection coating to improve its reflectivity. In this way, laser beams incident on the optical element 60x are substantially reflected and diffracted instead of transmitting therethrough, so that a larger amount of light returns to emitting points other than emitting points from which the laser beams are emitted, making laser beams phase-locked more efficiently.

Accordingly, all the laser beams emitted from the semiconductor laser array elements 11a, 11b, and 11c can be phase-locked as in the fourth embodiment. Furthermore, with the use of the optical element 60x having the diffraction grating, laser beams can be diffracted efficiently back to other emitting points of the semiconductor laser array element, or emitting points of other semiconductor laser array elements, ensuring phase-locking of the laser beams. Furthermore, as no optical element exists in front of the cleavage planes 122a, 122b, and 122c of the semiconductor laser array elements 11a, 11b, and 11c, laser beams emitted from this side can be condensed without any loss. As a result, output of higher power laser light can be achieved.

It should be noted that the present invention can also be realized when the incidence plane 61 of the optical element 60 is made flat as in the second embodiment, although diffraction efficiency of laser beams decreases in this case.

Also, at the side of the cleavage planes 122a, 122b, and 122c, such an optical element that is described in the third, fourth, and fifth embodiments may further be provided.

Seventh Embodiment

In the third to sixth embodiments, a plurality of semiconductor laser array elements are stacked in such a manner that emitting points thereof are in the same direction, so that laser beams emitted from the semiconductor laser array elements travel in the same direction. However, in the seventh embodiment, two semiconductor laser array elements are arranged facing each other in such a manner that emitting points thereof face each other. In this way, a laser beam emitted from an emitting point of one semiconductor laser array element is incident on an emitting point of the other semiconductor laser array element.

A multiple wavelength laser light emitting apparatus in the seventh embodiment has approximately the same construction as the multiple wavelength laser light emitting apparatus described in the first embodiment, with the only difference being in the form of its semiconductor laser devices. Accordingly, the following explains semiconductor laser devices in the seventh embodiment.

A semiconductor laser device that emits red laser beams and a semiconductor laser device that emits infrared laser beams are different only in the compositions of the semiconductor laser array elements, and therefore, the following only explains the semiconductor laser device 17x that emits red laser beams.

Figure 18:
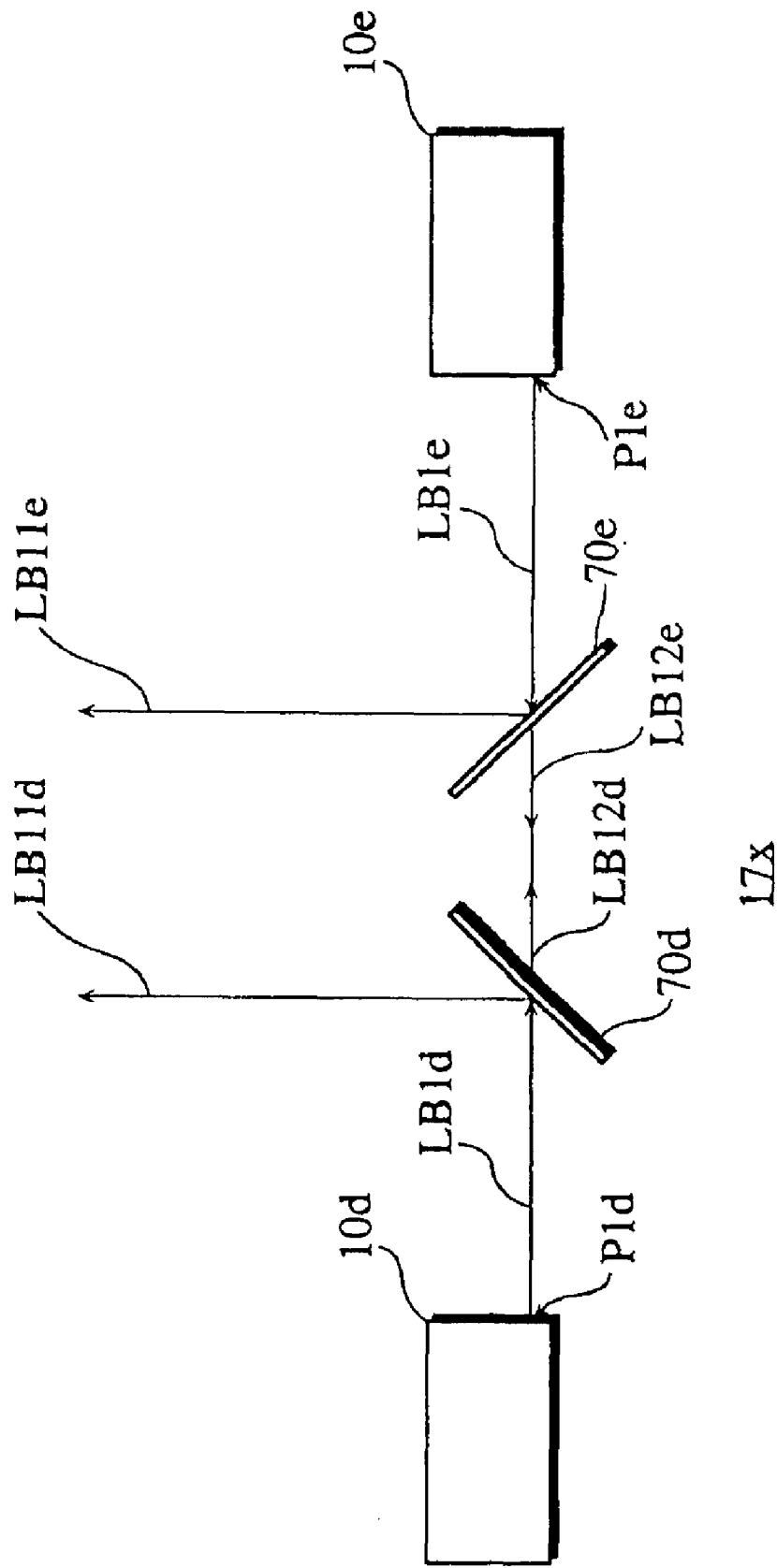
FIG. 18 is a side view of an overall construction of a semiconductor laser device relating to a seventh embodiment of the present invention.

FIG. 18 schematically shows the semiconductor laser device 17x in the seventh embodiment, showing its optical paths.

As shown in the figure, the semiconductor laser device 17x is composed of semiconductor laser array elements 10d and 10e, and optical elements 70d and 70e.

The semiconductor laser array elements 10d and 10e have the same construction, and are arranged in such a manner that respective emitting points P1d and P1e face each other, via the optical elements 70d and 70e. Laser beams LB1d and LB1e are respectively emitted from the emitting points P1d and P1e directed to the optical elements 70d and 70e.

The optical elements 70d and 70e are half mirrors that partially reflect incident laser beams LB1d and LB1e, whereas transmitting the remaining portions of the laser beams LB1d and lb1e. An incidence plane of each of the optical elements 70d and 70e is fixed with a supportive member (not illustrated) so as to form an angle of 45 degree with a chief ray of each of the laser beams LB1d and LB1e. With this construction, incident laser beams are partially reflected at an angle of 90 degree, and the reflected laser beams LB11d and LB11e travel toward the hologram optical element 2x shown in FIG. 1.

On the other hand, the laser beams LB12d and LB12e that have transmitted through the optical elements 70d and 70e are respectively incident on the optical elements 70e and 70d, where the laser beams LB12d and LB12e are again partially reflected, whereas the remaining portions are transmitted through the optical elements 70d and 70e. The laser beams that have transmitted through the optical elements 70d and 70e are respectively incident on the emitting points P1e and P1d. Here, each laser beam is incident on an emitting point that is not the emitting point from which the laser beam is originally emitted. As in the above embodiments, laser beams emitted from the semiconductor laser device 17x are also phase-locked. Due to this, a multiple wavelength laser light emitting apparatus employing such a semiconductor laser device can output laser light of high power.

It should be noted that the semiconductor laser array elements 10d and 10e used in the seventh embodiment each have a single emitting point, however, such a semiconductor laser array element that is described in the above embodiments, or a plurality of such semiconductor laser array elements being stacked up may be used to realize this invention. When a plurality of semiconductor laser array elements are used, is it preferable that emitting points of each of the semiconductor laser array elements are arranged with the same pitch, so that laser beams can be incident on emitting points of semiconductor laser array elements that face each other.

Modifications

Although the present invention has been described based on the above embodiment, the invention should not be limited to such. For instance, the following modifications are possible.

The above embodiments each explain a case where a semiconductor laser array element having a real refractive index guided self-aligned structure is employed, however, the present invention should not be limited to such. Any semiconductor laser device may be applicable to the present invention as long as it has a resonator. As examples, a plurality of single stripe semiconductor laser devices, or a plurality of surface emitting semiconductor laser devices may be used.

APPLICATION EXAMPLES

The following is an explanation of application examples of the multiple laser light emitting apparatus. Of course, the invention should not be limited to the following application examples.

Figure 19:
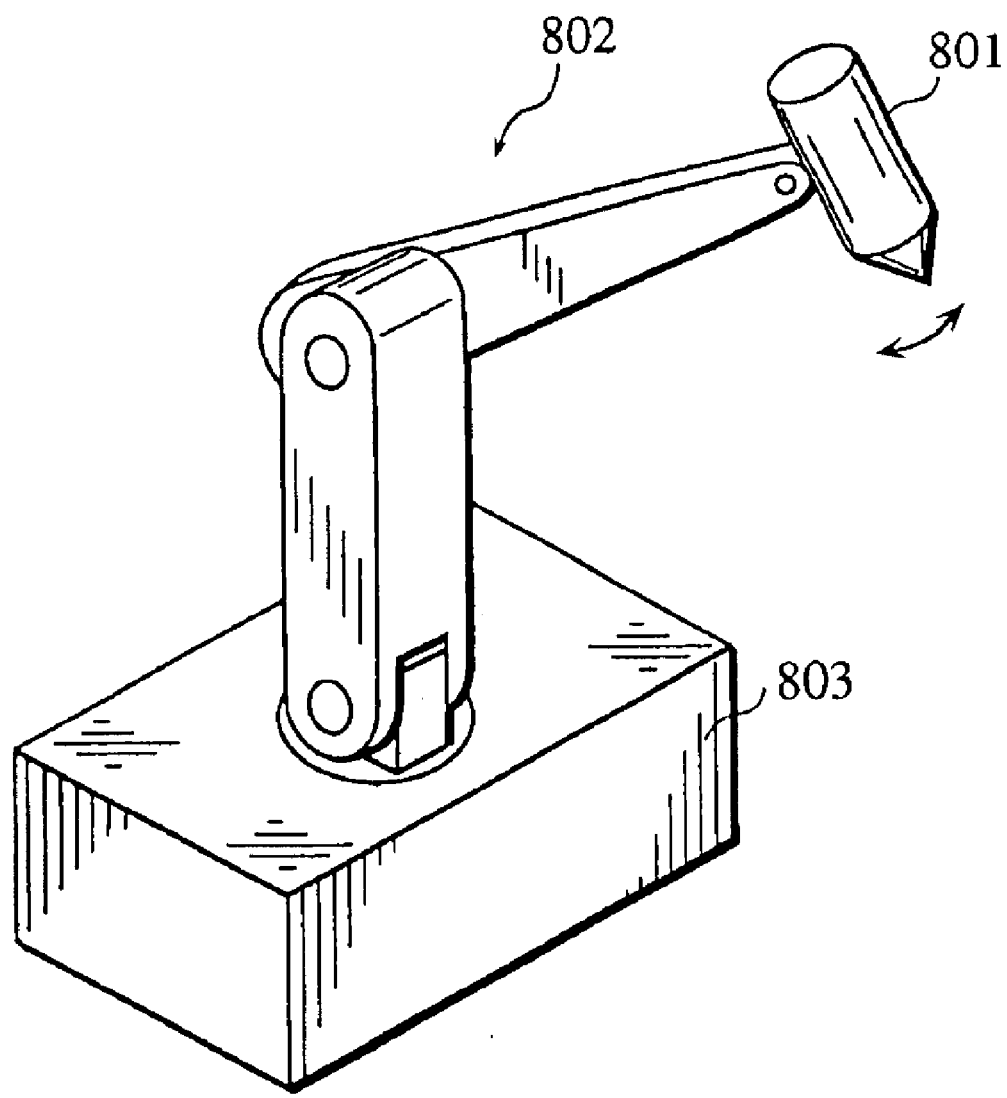
FIG. 19 is a perspective view of a conventional laser welding apparatus.

(1) The multiple wavelength laser light emitting apparatus may be mounted onto a torch for use in welding equipment, and used for welding materials. FIG. 19 is a perspective view of an appearance of a conventional welding robot 800. A laser welding torch 801 is held by a base 803 via a robot arm 802. The welding robot 800 welds a work according to a content programmed by a control unit (not illustrated). As its processing is not accurate enough, a typical method so called a weaving welding is employed. The weaving welding is to weld the work while periodically weaving the laser welding torch 801 in the direction shown by an arrow in the figure. Here, the laser welding torch 801 employing a conventional multiple wavelength laser light emitting apparatus is heavy in weight, and so the rigidity of the robot arm 802 should be increased so that the welding robot 800 itself does not sway due to the weaving operation of the laser welding torch 801. As a result, the welding robot is made large in size. On the other hand, the multiple wavelength laser light emitting apparatus of the present invention is constructed to be light in weight. If it is mounted on the laser welding torch 801, its weaving operation does not cause swaying of the welding robot 800 itself, and accordingly, the welding robot 800 can be downsized and can be made light in weight. Furthermore, a beam of light trembles when the optical axis of the condenser lens 4 in FIG. 1 or of the hologram optical element 4a in FIG. 2 is slightly shifted. Utilizing this, it becomes unnecessary to weave the laser welding torch 801 as shown in FIG. 19, and removes swaying of the welding robot 800 that puts an unfavorable effect on the processing accuracy. This construction has advantages not only because output of high power laser light is realized, but also the operation performance for welding can be improved as an operator can check his work if a laser beam in a visible area is used. Also, the multiple wavelength laser light emitting apparatus of the present invention is applicable to a punch press for punching or cutting printed circuit boards.

Such laser welding apparatuses mainly use a red laser made of AlGaInP (wavelength of 655 nm to 665 nm), or a infrared laser made of InGaAs (wavelength of 1060 nm; $In_{0.2}Ga_{0.8}As$). However, semiconductor laser array elements that emit laser beams of different wavelength may further be incorporated, so that types of laser beams can be switched to a laser beam with an appropriate wavelength according to a material of a work, thereby welding can be performed appropriately and rapidly without having to stop the welding processing.

This is particularly meaningful when a punching process is performed on a work made of at least two materials with different absorbencies. In such a case, the apparatus can apply laser beams with appropriate wavelengths suitable for each of the materials by switching types of laser beams in a short period, realizing an accurate punching process.

Also, making a laser beam scan a surface of a metal work, a surface transformation (quenching) can be made. In this case, too, output and wavelength of a laser beam may be changed according to a type of a metal to be processed. This makes the processing carried out efficiently.

(2) The present invention is also effective in producing dotted two-dimensional matrix data. As Japanese Laid-Open Patent Application No. H11-167602 discloses, an YAG laser has conventionally been used for this marking process. However, the problem is that the YAG laser is less responsive, and so it is difficult to form dots uniformly at high speed with the YAG laser. For example, the YAG laser is not suitable for forming such a matrix pattern that needs a laser beam to be applied with short pulses after a long interval. On the other hand, the multiple wavelength laser light emitting apparatus is superior in its responsiveness, and is effective in forming such a matrix pattern.

Also, as the multiple wavelength laser light emitting apparatus of the present invention can output laser beams with different wavelengths simply by switching the laser beam type, the following effect can be obtained. As one example, when the work onto which marking is applied is constructed by stitching different materials, a suitable laser beam can be applied to each of the materials simply by changing the laser beam type, at the interface of the two different materials, so that the marking can be performed on the work continuously. This greatly improves working efficiency. Also, when the work onto which marking is applied is constructed by laminating a plurality of members each having a different absorbency, a wavelength and output of laser beams can be selected for each of the layers, so that the apparatus can be more versatile. For example, marking or punching may be made only in the upper layer, or marking may be made only in the middle layer.

(3) the multiple wavelength laser light emitting apparatus is applicable not only to the field of industrial equipment as described above but also to the field of medical equipment.

For example, the multiple wavelength laser light emitting apparatus may be applied to medical equipment for a laser scalpel for an incision of a living body or for hemostasis, or may be applied to medical equipment for treatment of a malignant tumor, such as a cancer by applying a laser radiation to a body into which photofrin has been injected, or may be applied to medical equipment for hair restoration. Needless to say, suitable wavelengths are selected according to each purpose. In the multiple wavelength laser light emitting apparatus shown in FIG. 1 and FIG. 2, the laser beam type can be easily selected in terms of output and wavelength, and therefore, only a single apparatus is used for various purposes. It is also advantageous because an apparatus employing the multiple wavelength laser light emitting apparatus can be made small, occupying only a small space in a treatment room.

In particular, a blue laser made of InGaN (wavelength of 550 nm; $In_{0.5}Ga_{0.5}N$) is suitable for being applied to a retina for treatment of detachment of the retina. Also, a green laser (wavelength of 380 nm; $In_{0.05}Ga_{0.95}N$) is suitable for being applied to a cornea for treatment of myopia. Moreover, an infrared laser made of InGaAs (wavelength of 1060 nm; $In_{0.2}Ga_{0.8}As$) is suitable for being applied not only to a laser scalpel for an incision of a living body or for hemostasis but also to the treatment of detachment of the retina via an SHG element (an element decreases the wavelength by half) It should be noted that providing a single apparatus comprising a blue laser and a green laser, and selecting one of them when necessary greatly contributes to efficient treatment of eyes.

Although the present invention has been fully described byway of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. A semiconductor laser device comprising;
   a plurality of laser light oscillators that each emit a laser beam from a respective outlet;
   a diffraction grating with vertical and horizontal grooves that cross each other and that at least partially directs a sufficient portion of a laser beam from the plurality of laser light oscillators to enter another of the plurality of laser light oscillators to enable a phase locking of the respective laser light oscillators while transmitting the remaining portion of the laser beam, when the respective outlets of the laser light oscillators are aligned with the diffraction grating to enable each one of the laser light oscillators to receive at least a portion of the laser beam from another of the plurality of laser light oscillators to enable a phase locking of each one of the plurality of laser light oscillators, and
   one or more condenser lenses, wherein the one or more condenser lenses receives the laser beam emitted from an outlet portion of the diffraction grating and the diffracting grating is positioned optically between the plurality of laser light oscillators and the one or more condenser lenses.

2. The semiconductor laser device according to claim 1 wherein the diffraction grating is a flat plate.

3. The semiconductor laser device according to claim 1 wherein the diffraction grating includes a hologram to collimate portions of the laser beams transmitted therethrough.

4. The semiconductor laser device according to claim 1 wherein the laser light oscillators each have a refractive index guided self-aligned structure and are arranged parallel to each other.

5. The semiconductor laser device according to claim 4 wherein each of the laser light oscillators include GaInP/AlGaInP quantum well active layers.

6. The semiconductor laser device according to claim 1 wherein the diffraction grating directs between 10% to 30% of the incident laser beam to enter other laser light oscillators.

7. The semiconductor laser device according to claim 1 wherein the diffraction grating directs the sufficient portion of the laser beam at an optical axis of another laser light oscillator.

8. The semiconductor laser device of claim 1 wherein the plurality of laser light oscillators are arranged in a plurality of arrays, each array includes a plural number of laser light oscillators, the arrays are vertically stacked and the diffraction grating partially directs a sufficient portion of a plurality of laser beams from each array to enter laser light oscillators of other stacked arrays to enable a phase locking of all of the laser light oscillators.

9. A semiconductor laser device comprising:
   a plurality of laser light oscillators that each emit a laser beam from an outlet thereof;
   a diffraction grating that transmits a laser beam that is oscillated in at least one of the laser light oscillators and is emitted from an outlet thereof, so that a portion of the laser beam is incident on at least one of the other laser light oscillators,
   wherein the diffraction grating is a flat plate which includes the diffraction grating on a main surface thereof, the main surface being an incidence plane of the laser beam, and the flat plate partially diffracts the laser beam on the diffraction grating at a predetermined angle when the diffraction grating partially reflects the laser beam,
   wherein the diffraction grating directs −1st order diffracted light and +1st order diffracted light generated when the laser beam is partially diffracted, so as to be respectively incident on laser light oscillators that are adjacent to the at least one of the laser light oscillators from which the laser beam has been emitted, and
   one or more condenser lenses, wherein the one or more condenser lenses receives the laser beam emitted from an outlet portion of the diffraction grating and the diffracting grating is positioned optically between the plurality of laser light oscillators and the one or more condenser lenses, and the plurality of laser light oscillators are included in a semiconductor laser array element, and the diffraction grating is disposed so as to face the outlet of the at least one of the laser light oscillators, the diffraction grating being a translucent member that (a) partially transmits the laser beam and (b) partially reflects or scatters the laser beam so that a portion of the laser beam is directed to the at least one of the other laser light oscillators.

10. The semiconductor laser device according to claim 9 wherein the plurality of semiconductor laser array elements respectively include substrate layers that have been cut out of one semiconductor wafer.

11. The semiconductor laser device according to claim 9 wherein the plurality of semiconductor laser array elements each have a real refractive index guided self-aligned structure.

12. A semiconductor laser device comprising:

a plurality of laser light oscillators that each emit a laser beam from an outlet thereof;

a diffraction grating that transmits a laser beam that is oscillated in at least one of the laser light oscillators and is emitted from an outlet thereof, so that a portion of the laser beam is incident on at least one of the other laser light oscillators, wherein the diffraction grating is a flat plate which includes a diffraction grating on a main surface thereof, the main surface being an incidence plane of the laser beam, and the flat plate partially diffracts the laser beam on the diffraction grating at a predetermined angle when the diffraction grating partially reflects the laser beam, wherein the diffraction grating directs −1st order diffracted light and +1st order diffracted light generated when the laser beam is partially diffracted, so as to be respectively incident on laser light oscillators that are adjacent to the at least one of the laser light oscillators from which the laser beam has been emitted, and one or more condenser lenses, wherein the one or more condenser tenses receives the laser beam emitted from an outlet portion of the diffraction grating and the diffracting grating is positioned optically between the plurality of laser light oscillators and the one or more condenser lenses, and wherein the plurality of laser light oscillators are included in a plurality of semiconductor laser array elements in such a manner that at least two laser light oscillators are included in each laser light oscillator in an array, the plurality of semiconductor laser array elements being stacked up, and the diffraction grating is disposed so as to face the outlet of the at least one of the laser light oscillators included in one of the semiconductor laser array elements, the diffraction grating being a translucent member that (a) partially transmits the laser beam and (b) partially reflects or scatters the laser beam so that a portion of the laser beam is directed to the at least one of the other laser light oscillators included in the other semiconductor laser array elements.

* * * * *